(12) United States Patent
Hirata et al.

(10) Patent No.: US 8,236,969 B2
(45) Date of Patent: Aug. 7, 2012

(54) METHOD FOR PREPARING PROSTAGLANDIN DERIVATIVE

(75) Inventors: Ryu Hirata, Chiyoda-ku (JP); Tatsuya Matsukawa, Chiyoda-ku (JP); Kazuhiro Masuzaki, Chiyoda-ku (JP); Ryuji Ueno, Potomac, MD (US)

(73) Assignees: Sucampo AG, Zug (CH); R-Tech Ueno, Ltd., Tokyo (JP)

( * ) Notice: Subject to any disclaimer, the term of this patent is extended or adjusted under 35 U.S.C. 154(b) by 219 days.

(21) Appl. No.: 12/762,890

(22) Filed: Apr. 19, 2010

(65) Prior Publication Data
US 2010/0204491 A1    Aug. 12, 2010

Related U.S. Application Data

(62) Division of application No. 11/703,138, filed on Feb. 7, 2007, now Pat. No. 7,812,182.

(60) Provisional application No. 60/765,728, filed on Feb. 7, 2006.

(51) Int. Cl.
C07D 309/12    (2006.01)
C07F 7/18      (2006.01)

(52) U.S. Cl. ..................................... 549/214

(58) Field of Classification Search .................... 549/214
See application file for complete search history.

(56) References Cited

U.S. PATENT DOCUMENTS

| | | |
|---|---|---|
| 4,039,654 A | 8/1977 | Walker |
| 4,338,316 A | 7/1982 | Marsham |
| 5,229,529 A | 7/1993 | Ueno et al. |
| 5,284,858 A | 2/1994 | Ueno et al. |
| 5,468,880 A | 11/1995 | Ueno et al. |
| 5,739,161 A | 4/1998 | Ueno |
| 6,583,174 B1 | 6/2003 | Ueno et al. |
| 7,321,057 B2 | 1/2008 | Hirata et al. |

FOREIGN PATENT DOCUMENTS

| | | |
|---|---|---|
| EP | 0 643 051 A1 | 3/1995 |
| EP | 0643051 A1 | 3/1995 |
| WO | 94/07884 A1 | 4/1994 |
| WO | 97/31895 A2 | 9/1997 |

OTHER PUBLICATIONS

Roland et al.; A practical asymmetric synthesis of ent-12-PGF2α methyl ester; Bulletin de la Societe Chimique de France, 1996, vol. 133, No. 11, pp. 1149-1154.
Akhmetvaleev et al.; Prostanoids: LXXXI, Synthesis of (±)-2-Decarboxy-2-ethyl-19,20-dinor-18-carboxyprostaglandin E1, Russian Journal of Organic Chemistry (Translation of Zhurnal Organicheskoi Khimii), 2002, vol. 38, No. 3, pp. 361-364.
Kim et al.; The first total synthesis of iPF4α-VI and its deuterated analog; Tetrahedron Letters, 2002, vol. 43, No. 15, pp. 2801-2805.

*Primary Examiner* — Bernard Dentz
(74) *Attorney, Agent, or Firm* — Sughrue Mion, PLLC

(57) ABSTRACT

Disclosed is a method for preparing a prostaglandin derivative of formula (A):

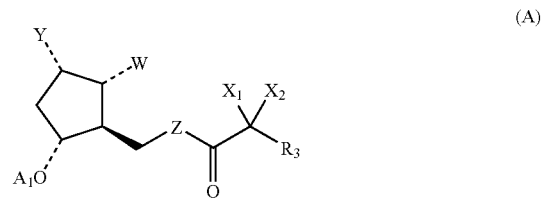

(A)

which comprises reacting an aldehyde represented by formula (1):

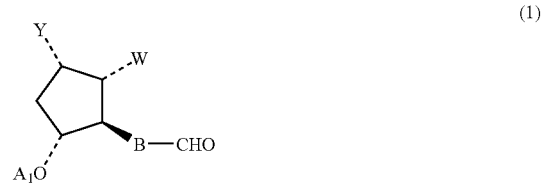

(1)

with a 2-oxoalkyl phosphonate in a reaction solvent under the presence of alkali hydroxide as sole base. By carrying out the reaction using an alkali hydroxide as sole base in the reaction system, the desired prostaglandin derivative can be obtained by simple procedures and with high yield.

2 Claims, No Drawings

METHOD FOR PREPARING PROSTAGLANDIN DERIVATIVE

CROSS REFERENCE TO RELATED APPLICATION

This is a divisional of application Ser. No. 11/703,138 filed Feb. 7, 2007, claiming benefit of Provisional Appln. No. 60/765,728 filed Feb. 7, 2006, the disclosures of which are incorporated herein by reference.

FIELD OF THE INVENTION

The present invention relates to a method for preparing a prostaglandin derivative that is useful for the treatment of a variety of diseases or conditions, or as synthesis intermediates for manufacturing therapeutically active compounds.

ART RELATED

Prostaglandin has a prostanoic acid structure indicated by the formula:

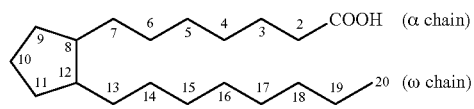

and there are many prostaglandins having a variety of therapeutic effects.

The Corey method is a conventional, well-known and representative method for prostaglandin synthesis.

The Corey method includes a process wherein an α,β-unsaturated ketolactone (III) is obtained from a Corey lactone (I) via a Corey aldehyde (II):

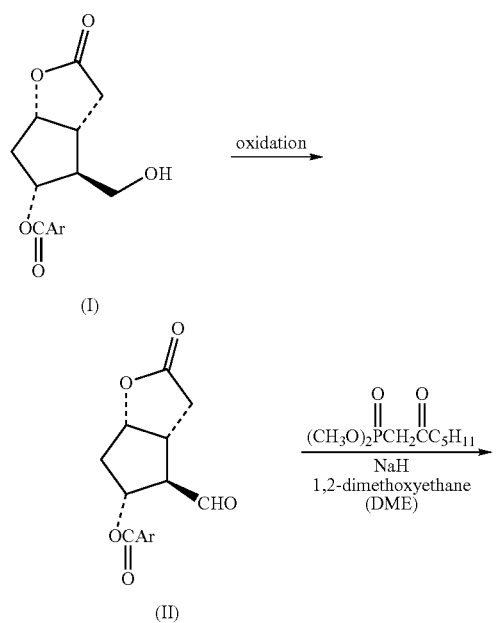

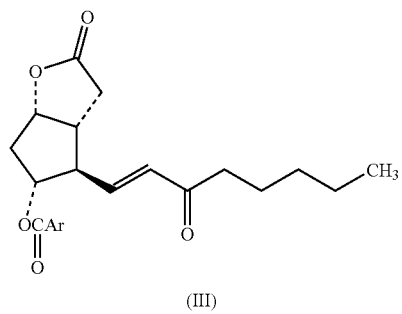

wherein Ar is an aromatic group.

That is to say, the Corey lactone (I) is oxidized to yield the Corey aldehyde (II), then reacted with an anion (enolate) prepared by the reaction of dimethyl 2-oxoalkyl phosphonate and sodium hydride, to give the α,β-unsaturated ketone (III).

In particular, when introducing an ω chain into an aldehyde in the process of synthesizing a prostaglandin compound having a halogen atom on the ω chain, it is difficult to ensure a sufficient yield for applying the method to the industrial use. Prostaglandin compounds having a halogen atom on the ω chain have therapeutic effects and the synthesis methods thereof have been studied (U.S. Pat. Nos. 6,583,174, 5,284,858 and 5,739,161, the contents of these references are herein incorporated by reference.).

Formerly, copper enolate and thallium enolate were tried to use to introduce an ω chain that was substituted with a halogen atom into the prostaglandin structure in high yield. However, the attempt using copper enolate failed to achieve sufficient yield. Although the attempt using thallium enolate could significantly increase the yield, thallium enolate was not preferably used in the industrial process owing to the toxicity of thallium per se and the high cost of thallium compounds.

Thereafter, an increase in yield has become possible by reacting in the presence of a base such as sodium hydride and a zinc compound (U.S. Pat. Nos. 5,229,529 and 5,468,880, the contents of these references are herewith incorporated by reference). This method requires metal exchange with zinc after preparation of the enolate from the phosphonate and the base, such that the cumbersomeness and complexity of the operational procedure has not been resolved. In addition, as the yield decreases by contamination of the reaction system with moisture, dehydration of the reaction solvent and drying of the zinc compound are mandatory. Moreover, as an industrial process, problems are still remained, such as, generation of liquid wastes containing zinc ion.

SUMMARY OF THE INVENTION

An object of the present invention is to provide a simple, highly efficient and industrially applicable method for preparing a prostaglandin derivative, especially, those having one or more halogen atoms on the ω chain.

Accordingly, the present invention provides a method for preparing a prostaglandin derivative of formula (A):

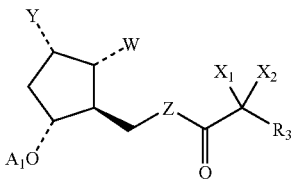

(A)

wherein $A_1$ is a hydrogen atom or a protecting group for a hydroxy group;

Y is —$OA_2$, wherein $A_2$ is a hydrogen or a protecting group for a hydroxy group;

W is —$R_1$-Q, wherein $R_1$ is a saturated or unsaturated bivalent lower or medium aliphatic hydrocarbon residue, which is unsubstituted or substituted with halogen, lower alkyl, hydroxy, oxo, aryl or heterocyclic, and at least one of carbon atoms in the aliphatic hydrocarbon is optionally substituted by oxygen, nitrogen or sulfur, Q is —$CH_3$, —$COCH_3$, —OH, —COOH or a functional derivative thereof; or Y and W may both together form a group represented by the formula:

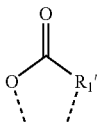

wherein $R_1'$ is a bivalent saturated or unsaturated lower to medium aliphatic hydrocarbon residue $R_3$ is a saturated or unsaturated lower to medium aliphatic hydrocarbon residue that is unsubstituted or substituted with a lower alkoxy, a lower alkanoyloxy, a cyclo(lower)alkyl, a cyclo(lower)alkyloxy, an aryl, an aryloxy, a heterocyclic or a heterocyclicoxy; a cyclo(lower)alkyl group; a cyclo(lower)alkyloxy group; an aryl group; an aryloxy group; a heterocyclic group; a heterocyclicoxy group;

$X_1$ and $X_2$ are a hydrogen, a lower alkyl group or a halogen; and

Z is =CH— or —CH=CH—, provided that —$OA_1$ and Q may together form

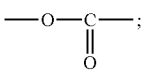

which comprises reacting an aldehyde represented by formula (1):

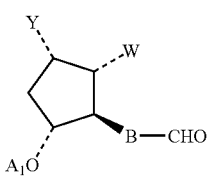

(1)

wherein Y, W and $A_1$ have the same meanings as above;

B is a single bond or —$CH_2$—, with a 2-oxoalkyl phosphonate represented by formula (2):

(2)

wherein $X_1$, $X_2$ and $R_3$ have the same meanings as above; and $R_2$ is a lower alkyl group;

in a reaction solvent under the presence of alkali hydroxide as sole base.

In another aspect of the present invention, the invention provides novel prostaglandin derivatives including:

7-[(1R,2R,3R,5S)-2-(4,4-difluoro-3-hydroxyoctyl)-5-hydroxy-3-(2-tetrahydropyranyloxy)cyclopentyl]heptanoic acid.

Benzyl 7-[(1R,2R,3R,5S)-2-(4,4-difluoro-3-hydroxy octyl)-5-hydroxy-3-(2-tetrahydropyranyloxy)cyclopentyl]heptanate.

Benzyl 7-[(1R,3R,6R,7R)-3-(1,1-difluoropentyl)-3-hydroxy-2-oxabicyclo[4.3.0]nonan-8-on-7-yl]heptanate.

Methyl 7-[(1R,2S,3R,5S)-2-(t-butyldimethylsilyloxy methyl)-5-hydroxy-3-(2-tetrahydropyranyloxy)cyclopentyl]heptanate.

Methyl 7-[(1R,2S,3R,5S)-5-acetoxy-2-(t-butyl dimethylsilyloxymethyl)-3-(2-tetrahydropyranyloxy)cyclopentyl]heptanate. Those compounds are useful for manufacturing a therapeutically effective prostaglandin derivative.

DETAILED DESCRIPTION OF THE PREFERRED EMBODIMENTS

In the above formulae, the term "unsaturated" in $R_1$, $R_1'$ and $R_3$ means to contain at least one or more double-bond and/or triple-bond alone, separately or contiguously, as bonds between carbon atoms of the main chain and/or side chain. According to the general nomenclature, unsaturations between two contiguous positions are indicated by representing the younger position number, and unsaturations between two non-contiguous positions are indicated by representing both position numbers.

The term "lower to medium aliphatic hydrocarbon" means a hydrocarbon having a straight or branched chain having 1 to 14 carbon atoms (for a side chain, 1 to 3 carbon atoms are preferable) and preferably 1 to 10, especially 6 to 10 carbon atoms for $R_1$; 1 to 10, especially, 1 to 6 carbon atoms for $R_1'$; and 1 to 10, especially 1 to 8 carbon atoms for $R_3$.

The term "halogen" comprises fluorine, chlorine, bromine and iodide.

The term "lower" comprises groups having 1 to 6 carbon atoms, unless specifically stated otherwise.

The term "lower alkyl" comprises straight chain or branched chain saturated hydrocarbon groups having 1 to carbon atoms, for instance, methyl, ethyl, propyl, isopropyl, butyl, isobutyl, sec-butyl, t-butyl, pentyl and hexyl.

The term "lower alkoxy" means lower alkyl-O—, in which lower alkyl has the same meaning as above.

The term "lower alkanoyloxy" means groups indicated by the formula RCO—O— (herein, RCO— is acyls generated by oxidation of lower alkyls such as those described above, for instance, acetyl).

The term "cyclo(lower)alkyl" comprises cyclic groups generated by cyclization of lower alkyl groups such as those described above, containing three or more carbon atoms, for instance, cyclopropyl, cyclobutyl, cyclopentyl and cyclohexyl.

The term "cyclo(lower)alkyloxy" means cyclo(lower)alkyl-O—, in which cyclo(lower)alkyl has the same meaning as above.

The term "aryl" comprises aromatic hydrocarbon ring group that may be unsubstituted or non-substituted, preferably monocyclic, for instance, phenyl, tolyl and xylyl can be given as examples. Substituents include halogens and halogen-substituted lower alkyl groups (herein, halogens and lower alkyl groups have the aforementioned meanings).

The term "aryloxy" means groups indicated by the formula ArO— (herein, Ar is aryl groups such as those described above).

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen, oxygen and sulfur. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen and lower alkyl group are as described above.

The term "heterocyclicoxy group" means a group represented by the formula HcO—, wherein Hc is a heterocyclic group as described above.

The term "functional derivative" for Q includes salts, preferably pharmaceutically acceptable salts, ethers, esters and amides.

As suitable "pharmaceutically acceptable salts", including non-toxic salts commonly used, salts with inorganic bases, for instance, alkaline metal salts (sodium salt, potassium salt and the like), alkaline earth metal salts (calcium salt, magnesium salt and the like), ammonium salts, salts with organic bases, for instance, amine salts (for instance, methylamine salt, dimethylamine salt, cyclohexyl amine salt, benzylamine salt, piperidine salt, ethylenediamine salt, ethanolamine salt, diethanolamine salt, triethanolamine salt, tris(hydroxymethyl amino)ethane salt, monomethyl-mono ethanolamine salt, procaine salt, caffeine salt and the like), basic amino acid salts (for instance, arginine salt, lysine salt and the like), tetra alkyl ammonium salts, and the like, can be given. These salts may be prepared, for instance, from corresponding acids and bases by a conventional reaction or salt exchange.

As examples of ethers, alkyl ethers, for instance, lower alkyl ethers, such as, methyl ether, ethyl ether, propyl ether, isopropyl ether, butyl ether, isobutyl ether, sec-butyl ether, t-butyl ether, pentyl ether and 1-cyclopropyl ethyl ether, medium or higher alkyl ethers, such as, octyl ether, diethyl hexyl ether, lauryl ether, cetyl ether, unsaturated ethers, such as, oleyl ether and linolenyl ether, lower alkenyl ethers, such as, vinyl ether and allyl ether, lower alkynyl ethers, such as, ethinyl ether and propynyl ether, hydroxy(lower)alkyl ethers, such as, hydroxyethyl ether and hydroxy isopropyl ether, lower alkoxy(lower)alkyl ethers, such as, methoxy methyl ether and 1-methoxy ethyl ether, and, for instance, optionally substituted aryl ethers, such as, phenyl ether, tosyl ether, t-butyl phenyl ether, salicyl ether, 3,4-dimethoxyphenyl ether and benzamide phenyl ether, and aryl(lower)alkyl ethers such as benzyl ether, trityl ether and benzhydryl ether, can be cited.

As esters, aliphatic esters including lower alkyl esters, such as, methyl ester, ethyl ester, propyl ester, isopropyl ester, butyl ester, isobutyl ester, sec-butyl ester, t-butyl ester, pentyl ester and 1-cyclopropyl ethyl ester, lower alkenyl esters, such as, vinyl ester and allyl ester, lower alkynyl esters, such as, ethinyl ester and propynyl ester, hydroxy (lower)alkyl esters, such as, hydroxyethyl ester, lower alkoxy (lower)alkyl esters, such as, methoxy methyl ester and 1-methoxy ethyl ester; and for instance, optionally substituted aryl esters, such as, phenyl ester, tolyl ester, t-butyl phenyl ester, salicyl ester, 3,4-dimethoxyphenyl ester and benzamide phenyl ester, and aryl (lower)alkyl esters such as, benzyl ester, trityl ester and benzhydryl ester can be cited.

The amides of Q means a group represented by the formula —CONR'R", wherein R' and R" are, respectively, a hydrogen, lower alkyl, aryl, alkyl- or aryl-sulfonyl, lower alkenyl and lower alkynyl, and for instance, lower alkyl amides, such as, methyl amide, ethyl amide, dimethylamide and diethylamide, aryl amides, such as, anilide and toluidide, alkyl- or aryl-sulfonyl amides, such as, methyl sulfonyl amide, ethyl sulfonyl amide and tolyl sulfonyl amide, and the like, can be cited.

Preferred examples for Q are —COOH, pharmaceutically acceptable salts, esters and amides thereof.

Preferred example for B is a single bond, and preferred example for Z is =CH—.

Preferred examples of $R_1$ are hydrocarbons having 1 to 10 carbon atoms, and especially, hydrocarbons having 6 to 10 carbon atoms. In addition, at least one carbon atom in the aliphatic hydrocarbon may be optionally substituted by an oxygen, a nitrogen or a sulfur.

Examples of $R_1$ include, for example, the following groups:

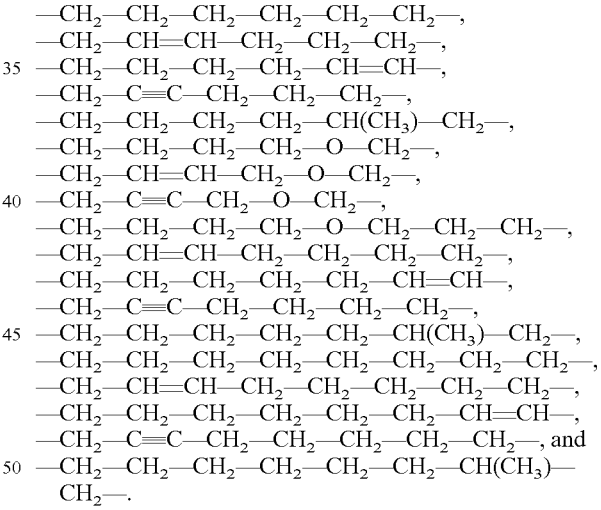

Preferred $R_3$ is an unsubstituted hydrocarbon having 1 to 10, and preferably 1 to 8 carbon atoms.

For $X_1$ and $X_2$, cases where at least one is a halogen are preferred, in particular, cases where both are halogen, especially fluorine, are preferred.

Examples of $A_1$ and $A_2$ may comprise the entirety of those groups forming protecting groups for hydroxy groups, and a protecting group for a hydroxy group means a functional group that is introduced to inactivate the hydroxy group against a specific reaction in order to avoid an undesirable chemical reaction, and as long as it conforms to this purpose, is not limited in particular. For instance, methyl group, methoxy methyl group, ethyl group, 1-ethoxy ethyl group, benzyl group, substituted benzyl group, allyl group, tetrapyranyl group, t-butyl dimethyl silyl group, triethyl silyl group, triisopropyl silyl group, diphenyl methyl silyl group, formyl group, acetyl group, substituted acetyl group, benzoyl group, substituted benzoyl group, methyloxy carbonyl group, benzyloxy carbonyl group, t-butyloxy carbonyl group, allyloxy carbonyl group, and the like, can be cited.

According to the present invention, a method for preparing a prostaglandin derivative, especially, a prostaglandin derivative having one or more halogen on the ω chain represented by formula (A) is obtained by reacting an aldehyde (1) and a 2-oxoalkylphosphonate (2) in the presence of an alkali hydroxide as sole base in the reaction system.

In a preferred embodiment, a prostaglandin derivative represented by formula (B):

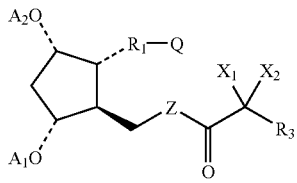

(B)

may be prepared using an aldehyde represented by formula (3):

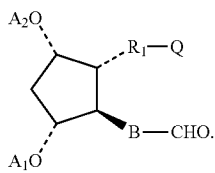

(3)

wherein $A_1$, $A_2$, B, $R_1$, Q, $X_1$, $X_2$ and Z have the same meanings as described above.

In preferred embodiment, a prostaglandin derivative of formula (C):

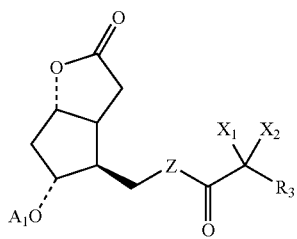

(C)

may be prepared using an aldehyde of formula (4):

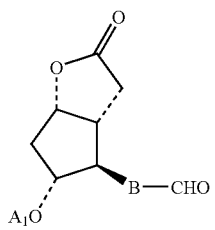

(4)

wherein $A_1$, B, $R_3$, $X_1$, $X_2$ and Z have the same meanings as described above.

By carrying out the reaction using an alkali hydroxide as sole base in the reaction system, the target product, prostaglandin derivative can be obtained in high yield by simple procedures. There is no need to use a heavy metal reagent like zinc compound. On the other hand, for instance when a base such as alkaline metal hydroxide is used alone, prostaglandin derivative having a halogen atom on the ω chain, in particular, cannot be obtained effectively.

According to the present invention, alkali hydroxide may be any of those shown by the formula:

$$M\text{-}OH \text{ or } M(OH)_2;$$

wherein M is an alkaline metal or an alkaline earth metal. In more detail, lithium hydroxide, sodium hydroxide, potassium hydroxide, calcium hydroxide, strontium hydroxide, barium hydroxide, and the like, can be cited, and preferably lithium hydroxide may be used.

The amount of alkali hydroxide used is preferably on the order of 0.9 to 1 equivalent with respect to 2-oxoalkyl phosphonate represented by formula (2). In addition, the amount of 2-oxoalkyl phosphonate (2) used in the reaction is preferably on the order of 1 to 3 equivalents with respect to the aldehyde represented by formula (1), and especially, on the order of 1.1 to 2 equivalents.

The reaction solvent is not limited in particular, and for instance, ethers, such as, ethyl ether, dimethoxy ethane, t-butyl methyl ether, diisopropyl ether, tetrahydrofuran and dioxane, aromatic compounds, such as, benzene and toluene, and halogenated hydrocarbons such as dichloroethane are preferred, and ethers are particularly preferred.

The amount of reaction solvent used in the reaction may be 1 to 100 ml with respect to 1 g of aldehyde (1), and especially, 10 to 50 ml.

The reaction temperature may be 0 to 100° C., and especially, 20 to 80° C.

The reaction time may be 1 to 100 hours, especially 10 to 50 hours when at least one of $X_1$ and $X_2$ is a halogen, in particular a fluorine, and especially, 1 to 5 hours extent when $X_1$ and $X_2$ are other than halogen.

According to the invention, the reaction system may comprise water. The amount of water added to the reaction may be 0.5 to 10% with respect to the reaction solvent, and especially, of 1 to 4%.

EXAMPLES

The present invention will be explained in more detail by means of the following examples, which are illustrated by way of example only and never intended to limit the scope of the present invention.

Example 1a

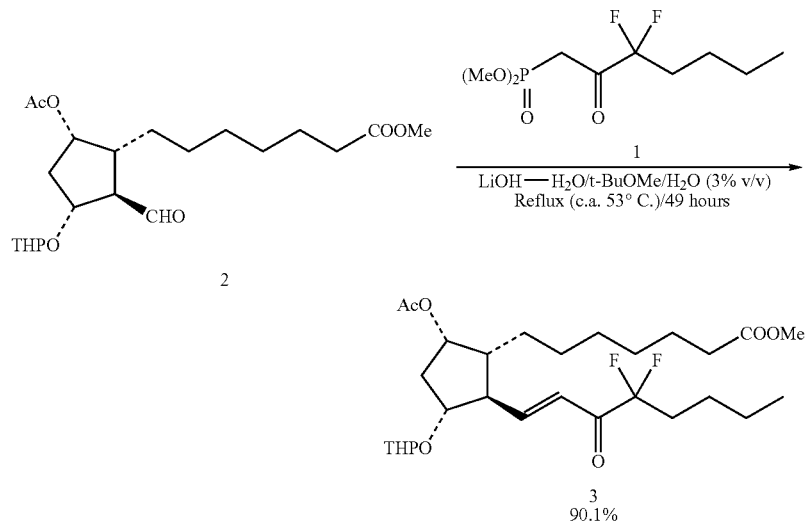

To a solution of dimethyl(3,3-difluoro-2-oxoheptyl)phosphonate (1) (50.50 g, 195.6 mmol) in t-butyl methyl ether (750 ml), lithium hydroxide monohydrate (7.94 g, 189 mmol) was added and the mixture was stirred for one hour at room temperature. A solution of methyl 7-[(1R,2R,3R,5S)-5-acetoxy-2-formyl-3-(2-tetrahydropyranyloxy)cyclopentyl]heptanate (2) (52.00 g, 130.5 mmol) in t-butyl methyl ether (150 ml) and water (27 ml) were added thereto, and the mixture was heat refluxed for approximately 49 hours (internal temperature: approximately 53° C.). After cooling to room temperature, water (300 ml) was added and the mixture was stirred, let to stand and then separated into two layers. The aqueous layer was extracted twice with ethyl acetate (200 ml). The organic layers were combined, washed twice with saturated aqueous sodium chloride (300 ml), and dried with anhydrous magnesium sulfate (50 g). After concentration under reduced pressure, the residue was purified by silica gel column chromatography (Fuji Silysia BW-300: 1805 g; ethyl acetate:hexane =1:4). The fractions containing impurities were re-purified by silica gel column chromatography (Fuji Silysia BW-300: 580 g; ethyl acetate:hexane =1:4), to give methyl 7-[(1R,2R,3R,5S)-5-acetoxy-2-((E)-4,4-difluoro-3-oxo-1-octenyl)-3-(2-tetrahydropyranyloxy)cyclopentyl]heptanate (3) (62.38 g; 117.6 mmol; yield: 90.1%) as a pale yellow oil.

$^1$H-NMR (200 MHz, CDCl$_3$): δ (ppm): 7.10 (0.5H, dd, J=15.7, 7.0 Hz), 7.05 (0.5H, dd, J=15.7, 7.4 Hz), 6.67 (0.5H, d, J=15.7 Hz), 6.62 (0.5H, d, J=15.7 Hz), 5.19-5.08 (1H, m), 4.61-4.46 (1H, m), 4.18-3.93 (1H, m), 3.88-3.62 (1H, m), 3.66 (3H, s), 3.51-3.31 (1H, m), 2.87-2.36 (2H, m), 2.29 (2H, t, J=7.4 Hz), 2.15-1.11 (24H, m), 2.07 (3H, s), 0.92 (3H, t, J=6.9 Hz)

Example 1b

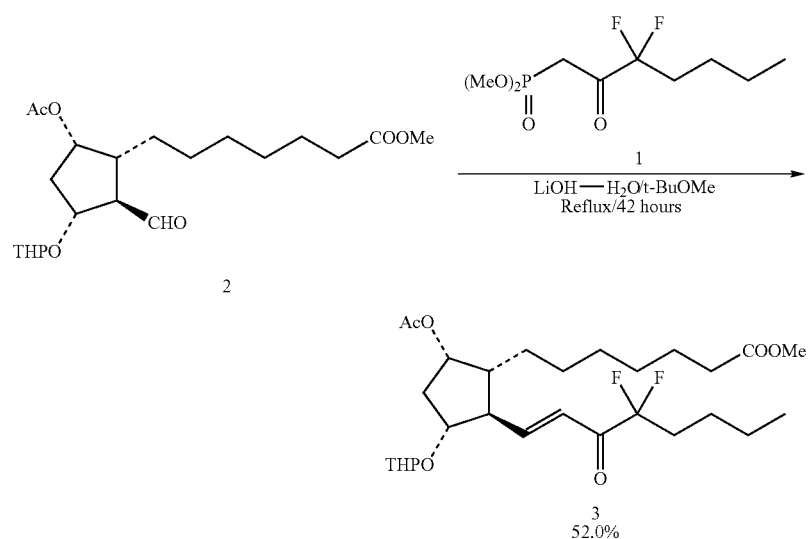

To a solution of dimethyl (3,3-difluoro-2-oxoheptyl)phosphonate (1) (0.243 g, 941 mmol) in t-butyl methyl ether (4 ml), lithium hydroxide monohydrate (38.2 mg, 910 mmol) was added and the mixture was stirred for one hour at room temperature. A solution of methyl 7-[(1R,2R,3R,5S)-5-acetoxy-2-formyl-3-(2-tetrahydropyranyloxy)cyclopentyl]heptanate (2) (0.250 g, 627 mmol) in t-butyl methyl ether (3 ml) was added thereto, and the mixed solution was heat refluxed for approximately 42 hours. After cooling to room temperature, the reaction mixture was added to water and extracted twice with t-butyl methyl ether. The organic layers were combined, sequentially washed with saturated sodium bicarbonate water and saturated aqueous sodium chloride, and then dried with anhydrous magnesium sulfate. After concentration under reduced pressure, the residue was purified by silica gel column chromatography (Fuji Silysia FL-60D: 100 g; ethyl acetate:hexane =1:3), to give methyl 7-[(1R,2R,3R,5S)-5-acetoxy-2-((E)-4,4-difluoro-3-oxo-1-octenyl)-3-(2-tetrahydropyranyloxy)cyclopentyl]heptanate (3) (0.173 g; 326 mmol; yield: 52.0%).

To a solution of dimethyl (3,3-difluoro-2-oxoheptyl)phosphonate (1) (1.051 g, 4.070 mmol) in anhydrous t-butyl methyl ether (16 ml), lithium hydride (30.3 mg, 3.81 mmol) was added and the mixture was stirred for approximately 6 hours at room temperature. A solution of methyl 7-[(1R,2R,3R,5S)-5-acetoxy-2-formyl-3-(2-tetrahydro pyranyloxy)cyclopentyl]heptanate (2) (0.903 g, 2.27 mmol) in anhydrous t-butyl methyl ether (3 ml) was added thereto, and the mixed solution was heat refluxed for approximately 48 hours. After cooling to room temperature, water was added to the solution and the mixture was stirred, let to stand and then separated into two layers. The aqueous layer was extracted twice with ethyl acetate. The organic layers were combined, sequentially washed with 3% aqueous sodium chloride and saturated aqueous sodium chloride, and then dried with anhydrous magnesium sulfate. After concentration under reduced pressure, the residue was purified by silica gel column chromatography (Fuji Silysia BW-300SP: 36 g/15 g/18 g; ethyl acetate:hexane =1:4) three times, to give methyl 7-[(1R,2R,3R,5S)-5-acetoxy-2-((E)-4,4-difluoro-3-oxo-1-octenyl)-3-

Comparative Example 1

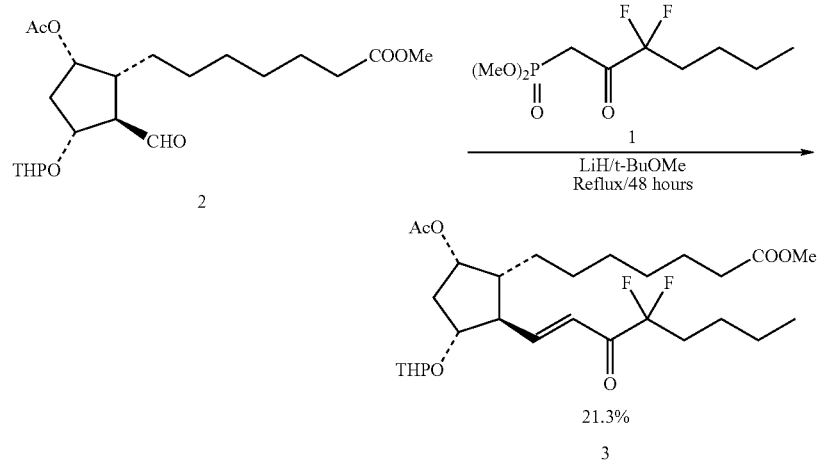

(2-tetrahydropyranyloxy)cyclopentyl]heptanate (3) (0.257 g; 0.484 mmol; yield: 21.3%).

Example 2a

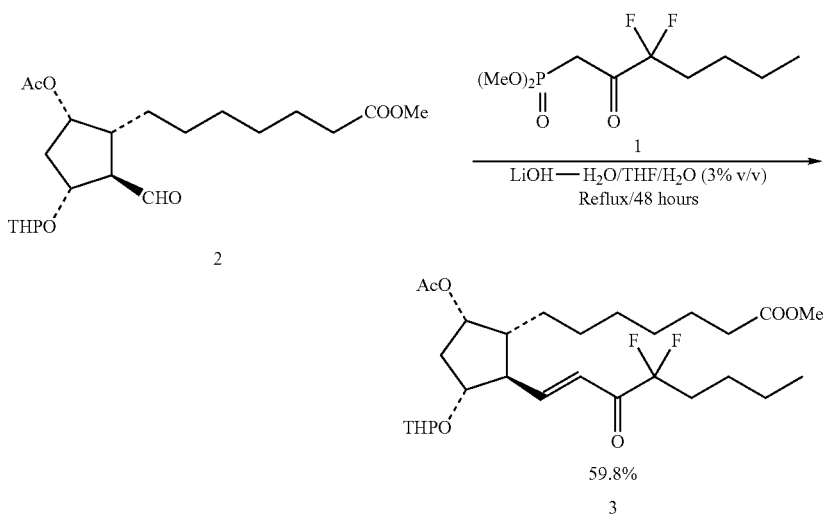

To a solution of dimethyl (3,3-difluoro-2-oxoheptyl)phosphonate (1) (1.050 g, 4.066 mmol) in tetrahydrofuran (16 ml), lithium hydroxide monohydrate (0.161 g, 3.84 mmol) was added and the mixture was stirred at room temperature for approximately 1.2 hours. A solution of methyl 7-[(1R,2R,3R,5S)-5-acetoxy-2-formyl-3-(2-tetrahydropyranyloxy)cyclopentyl]heptanate (2) (0.903 g, 2.27 mmol) in tetrahydrofuran (3 ml), and water (0.57 ml) were added thereto, and the mixed solution was heat refluxed for approximately 48 hours. After cooling to room temperature, approximately half of the solvent was evaporated from the solution under reduced pressure. Ethyl acetate and water were added to the solution and the solution was stirred, let to stand and then separated into two layers. The aqueous layer was extracted twice with ethyl acetate. The organic layers were combined, sequentially washed with 3% aqueous sodium chloride and saturated aqueous sodium chloride, and then dried with anhydrous magnesium sulfate. After concentration under reduced pressure, the residue was purified by silica gel column chromatography (Fuji Silysia BW-300SP 27 g, ethyl acetate:hexane = 1:4). The fractions containing impurities were re-purified by silica gel column chromatography (Fuji Silysia BW-300SP: 6 g; ethyl acetate:hexane=1:4), to give methyl 7-[(1R,2R,3R,5S)-5-acetoxy-2-((E)-4,4-difluoro-3-oxo-1-octenyl)-3-(2-tetrahydropyranyloxy)cyclopentyl]heptanate (3) (0.719 g; 1.35 mmol; yield: 59.8%).

Example 2b

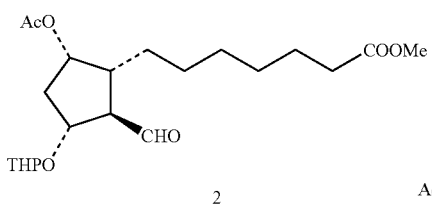
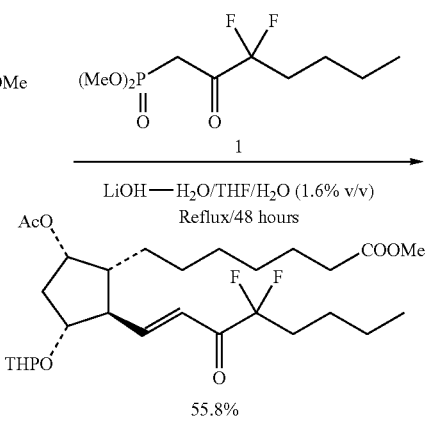

A solution of dimethyl (3,3-difluoro-2-oxoheptyl)phosphonate (1) (1.110 g, 4.299 mmol) in tetrahydrofuran (17 ml) was added with lithium hydroxide monohydrate (0.171 g, 4.08 mmol), and the mixture was stirred for approximately 1.2 hours at room temperature. A solution of methyl 7-[(1R,2R,3R,5S)-5-acetoxy-2-formyl-3-(2-tetrahydro pyranyloxy)cyclopentyl]heptanate (2) (0.971 g, 2.44 mmol) in tetrahydrofuran (3 ml), and water (0.32 ml) were added thereto, and the mixed solution was heat refluxed for approximately 48 hours. After cooling to room temperature, the solution was concentrated under reduced pressure. Ethyl acetate and water were added to the residue and the solution was stirred, let to stand and then separated into two layers. The aqueous layer was extracted twice with ethyl acetate. The organic layers were combined, sequentially washed with 3% aqueous sodium chloride and saturated aqueous sodium chloride, and then dried with anhydrous magnesium sulfate. After concentration under reduced pressure, the residue was purified by silica gel column chromatography (Fuji Silysia BW-300SP: 38 g; ethyl acetate:hexane =1:4), to give methyl 7-[(1R,2R,3R,5S)-5-acetoxy-2-((E)-4,4-difluoro-3-oxo-1-octenyl)-3-(2-tetrahydropyranyloxy)cyclopentyl]heptanate (3) (0.722 g; 1.36 mmol; yield: 55.8%).

Example 2c

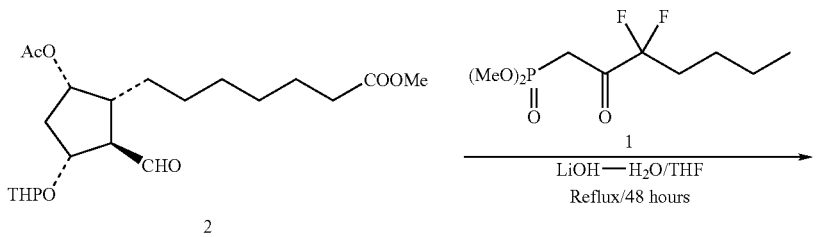

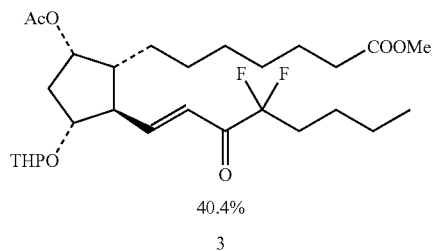

40.4%

3

A solution of dimethyl (3,3-difluoro-2-oxoheptyl)phosphonate (1) (1.110 g, 4.299 mmol) in tetrahydrofuran (17 ml) was added with lithium hydroxide monohydrate (0.171 g, 4.08 mmol), and the mixture was stirred for approximately 1.2 hours at room temperature. A solution of methyl 7-[(1R, 2R,3R,5S)-5-acetoxy-2-formyl-3-(2-tetrahydropyranyloxy) cyclopentyl]heptanate (2) (0.962 g, 2.41 mmol) in tetrahydrofuran (3 ml) was added thereto, and the mixed solution was heat refluxed for approximately 48 hours. After cooling to room temperature, the solution was concentrated under reduced pressure. Ethyl acetate and water were added to the residue and stirred, then, the mixture was let to stand and separated into two layers. The aqueous layer was extracted twice with ethyl acetate. The organic layers were combined, sequentially washed with 3% aqueous sodium chloride and saturated aqueous sodium chloride, and then dried with anhydrous magnesium sulfate. After concentration under reduced pressure, the residue was purified by silica gel column chromatography (Fuji Silysia BW-300SP: 38 g; ethyl acetate: hexane =1:4), to give methyl 7-[(1R,2R,3R,5S)-5-acetoxy-2-((E)-4,4-difluoro-3-oxo-1-octenyl)-3-(2-tetrahydropyranyloxy)cyclopentyl]heptanate (3) (0.517 g; 0.973 mmol; yield: 40.4%).

To a solution of dimethyl (3,3-difluoro-2-oxoheptyl)phosphonate (1) (0.453 g, 1.75 mmol) in anhydrous THF (7 ml), sodium hydride (60%, dispersion in mineral oil, 70 mg, 1.75 mmol) was added and stirred for 15 minutes at room temperature. A solution of methyl 7-[(1R,2R,3R,5S)-5-acetoxy-2-formyl-3-(2-tetrahydropyranyloxy)cyclopentyl]heptanate (2) (0.175 g, 439 mmol) in anhydrous THF (3 ml) was added thereto, and the mixed solution was heat refluxed for approximately 4 hours. Only a trace amount of the target product (3) was obtained.

Comparative Example 2

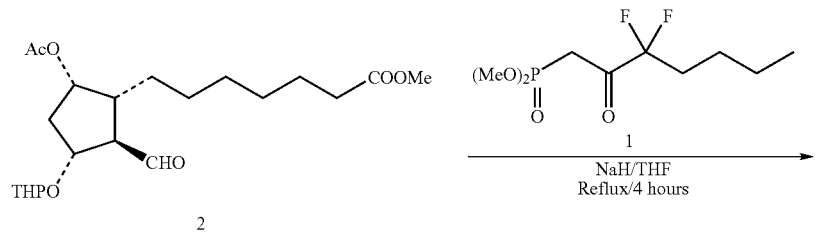

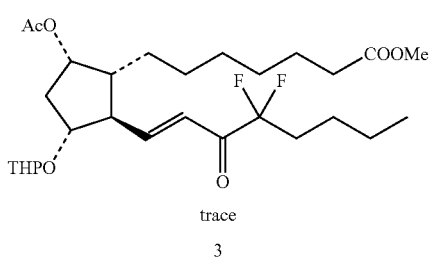

trace

3

Example 3

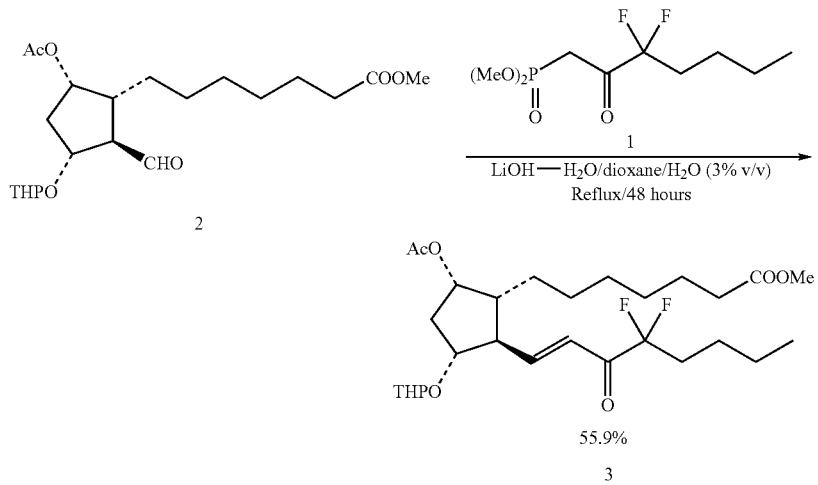

To a solution of dimethyl (3,3-difluoro-2-oxoheptyl)phosphonate (1) (1.052 g, 4.074 mmol) in 1,4-dioxane (16 ml), lithium hydroxide monohydrate (0.160 g, 3.81 mmol) was added and stirred for approximately 1.2 hours at room temperature. A solution of methyl 7-[(1R,2R,3R,5S)-5-acetoxy-2-formyl-3-(2-tetrahydro pyranyloxy)cyclopentyl]heptanate (2) (0.902 g, 2.26 mmol) in 1,4-dioxane (3 ml) and water (0.57 ml) were added thereto, and the mixed solution was heat refluxed for approximately 48 hours. After cooling to room temperature, approximately half of the solvent was evaporated under reduced pressure. Ethyl acetate and water were added to the residue and the solution was stirred, let to stand and then separated into two layers. The aqueous layer was extracted twice with ethyl acetate. The organic layers were combined, sequentially washed with 3% aqueous sodium chloride and saturated aqueous sodium chloride, and then dried with anhydrous magnesium sulfate. After concentration under reduced pressure, the residue was purified by silica gel column chromatography (Fuji Silysia BW-300SP: 36 g; ethyl acetate:hexane =1:4). The fractions containing impurities were re-purified by silica gel column chromatography (Fuji Silysia BW-300SP: 6 g; ethyl acetate:hexane =1:4) to give methyl 7-[(1R,2R,3R,5S)-5-acetoxy-2-((E)-4,4-difluoro-3-oxo-1-octenyl)-3-(2-tetrahydropyranyloxy)cyclopentyl]heptanate (3) (0.671 g; 1.26 mmol; yield: 55.9%).

Example 4a

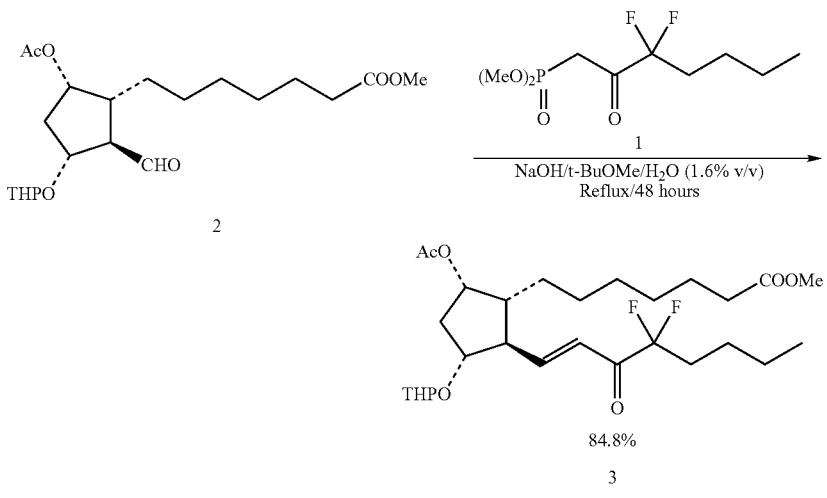

To a solution of dimethyl (3,3-difluoro-2-oxoheptyl)phosphonate (1) (1.109 g, 4.295 mmol) in t-butyl methyl ether (17 ml), sodium hydroxide (0.164 g, 4.10 mmol) was added and the mixture was stirred for approximately 1.2 hours at room temperature. A solution of methyl 7-[(1R,2R,3R,5S)-5-acetoxy-2-formyl-3-(2-tetrahydropyranyloxy)cyclopentyl] heptanate (2) (0.955 g, 2.40 mmol) in t-butyl methyl ether (3 ml), and water (0.32 ml) were added thereto, and the mixed solution was heat refluxed for approximately 48 hours. After cooling to room temperature, water (5.6 ml) was added to the solution and stirred, and then, let to stand and separated into two layers. The aqueous layer was extracted twice with ethyl acetate (4 ml). The organic layers were combined, sequentially washed with 3% aqueous sodium chloride (6 ml) and saturated aqueous sodium chloride (6 ml), and then dried with anhydrous magnesium sulfate. After concentration under reduced pressure, the residue was purified by silica gel column chromatography (Fuji Silysia BW-300SP: 33 g; ethyl acetate:hexane =1:4) to give methyl 7-[(1R,2R,3R,5S)-5-acetoxy-2-((E)-4,4-difluoro-3-oxo-1-octenyl)-3-(2-tetrahydropyranyloxy)cyclopentyl]heptanate (3) (1.079 g; 2.033 mmol; yield: 84.8%).

Example 4b

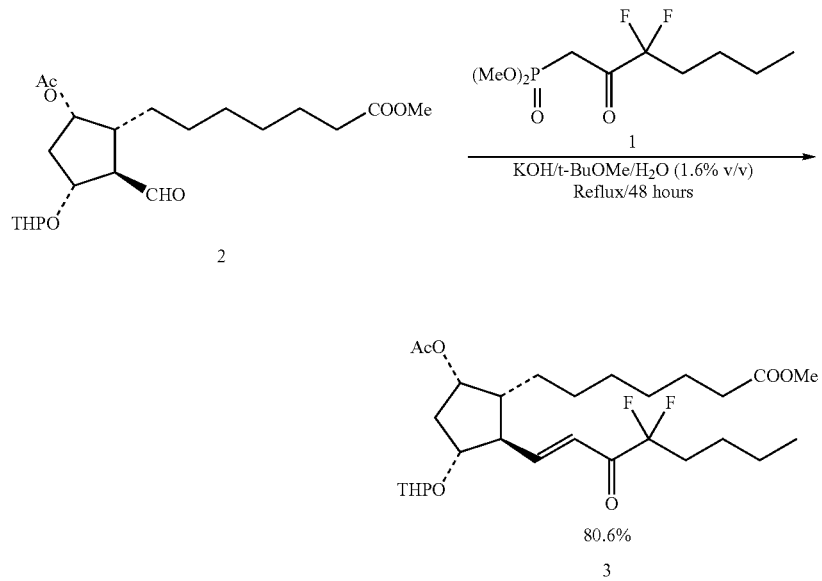

To a solution of dimethyl (3,3-difluoro-2-oxoheptyl)phosphonate (1) (1.113 g, 4.31 mmol) in t-butyl methyl ether (17 ml), potassium hydroxide (0.225 g, 4.00 mmol) was added and the mixture was stirred for approximately 1.2 hours at room temperature. A solution of methyl 7-[(1R,2R,3R,5S)-5-acetoxy-2-formyl-3-(2-tetrahydro pyranyloxy)cyclopentyl]heptanate (2) (0.965 g, 2.42 mmol) in t-butyl methyl ether (3 ml) solution, and water (0.32 ml) were added thereto. The mixed solution was heat refluxed for approximately 48 hours. After cooling to room temperature, water (5.6 ml) was added to the solution and the mixture was stirred, let to stand and then separated into two layers. The aqueous layer was extracted twice with ethyl acetate (4 ml). The organic layers were combined, sequentially washed with 3% aqueous sodium chloride (6 ml) and saturated aqueous sodium chloride (6 ml), and dried with anhydrous magnesium sulfate. After concentration under reduced pressure, the residue was purified by silica gel column chromatography (Fuji Silysia BW-300SP: 33 g; ethyl acetate:hexane =1:4) to give methyl 7-[(1R,2R,3R,5S)-5-acetoxy-2-((E)-4,4-difluoro-3-oxo-1-octenyl)-3-(2-tetrahydropyranyloxy)cyclopentyl]heptanate (3) (1.035 g; 1.950 mmol; yield: 80.6%).

Example 5a

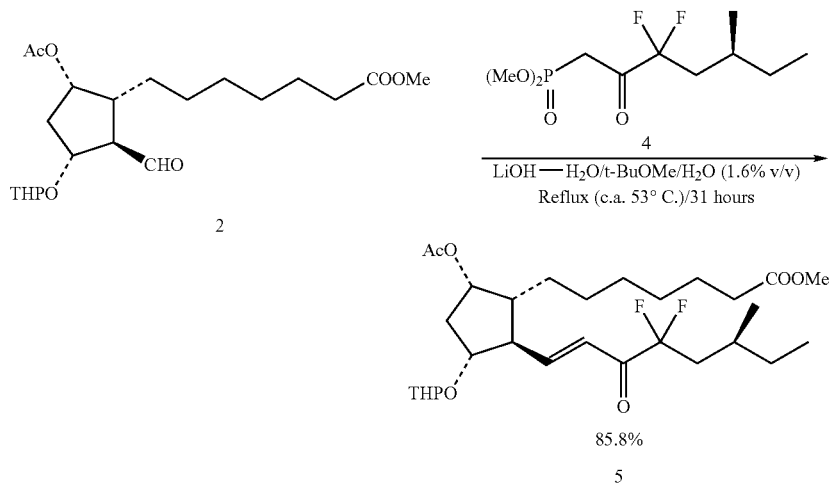

To a solution of dimethyl (3,3-difluoro-5S-methyl-2-oxo-heptyl)phosphonate (4) (74.7 g, 274 mmol) in t-butyl methyl ether (1120 ml), lithium hydroxide monohydrate (11.5 g, 273 mmol) was added and the mixture was stirred for one hour at room temperature. A solution of methyl 7-[(1R,2R,3R,5S)-5-acetoxy-2-formyl-3-(2-tetrahydropyranyloxy)cyclopentyl]heptanate (2) (64.02 g, 160.6 mmol) in t-butyl methyl ether (278 ml) and water (21.7 ml) were added thereto, and the mixed solution was heat refluxed for approximately 31 hours (internal temperature: approximately 53° C.). After cooling to room temperature, water (351 ml) was added to the solution and the mixture was stirred, let to stand and then separated into two layers. The aqueous layer was extracted twice with ethyl acetate (234 ml). The organic layers were combined, washed twice with saturated aqueous sodium chloride (351 ml), and dried with anhydrous magnesium sulfate (55 g). After concentration under reduced pressure, the residue was purified by silica gel column chromatography (Fuji Silysia BW-300: 2110 g; ethyl acetate:hexane =1:4 to 1:2). The fractions containing impurities were re-purified by silica gel column chromatography (Fuji Silysia BW-300: 850 g; ethyl acetate:hexane =1:4 to 1:2) to give methyl 7-[(1R,2R,3R,5S)-5-acetoxy-2-((E)-4,4-difluoro-6S-methyl-3-oxo-1-octenyl)-3-(2-tetrahydropyranyloxy)cyclopentyl]heptanate (5) (75.03 g; 137.8 mmol; yield: 85.8%) as a pale yellow oil.

$^1$H-NMR (200 MHz, CDCl$_3$): δ (ppm): 7.10 (0.5H, dd, J=15.6, 6.5 Hz), 7.05 (0.5H, dd, J=15.6, 7.0 Hz), 6.68 (0.5H, d, J=15.6 Hz), 6.63 (0.5H, d, J=15.6 Hz), 5.19-5.09 (1H, m), 4.61-4.46 (1H, m), 4.19-3.93 (1H, m), 3.88-3.60 (1H, m), 3.66 (3H, s), 3.50-3.31 (1H, m), 2.87-2.36 (2H, m), 2.28 (2H, t, J=7.5 Hz), 2.15-1.03 (23H, m), 2.07 (3H, s), 0.97 (3H, t, J=6.4 Hz), 0.88 (3H, t, J=7.3 Hz)

Example 5b

To a solution of dimethyl (3,3-difluoro-2-oxo-3-phenyl-propyl)phosphonate (6) (0.262 g, 0.942 mmol) in t-butyl methyl ether (7 ml), lithium hydroxide monohydrate (38.2 mg, 0.910 mmol) was added and the mixture was stirred for one hour at room temperature. A solution of methyl 7-[(1R, 2R,3R,5S)-5-acetoxy-2-formyl-3-(2-tetrahydropyranyloxy) cyclopentyl]heptanate (2) (0.250 g, 0.627 mmol) in t-butyl methyl ether (3 ml) and water (0.3 ml) were added thereto, and the mixed solution was heat refluxed for approximately 48 hours. After cooling to room temperature, the reaction mixture was added to water, and extracted twice with t-butyl methyl ether. The organic layers were combined, sequentially washed with water, saturated sodium bicarbonate water and saturated aqueous sodium chloride, and then dried with anhydrous magnesium sulfate. After concentration under reduced pressure, the residue was purified by silica gel column chromatography (Merck Art. 9385: 200 g; ethyl acetate: hexane =2:3). The fractions containing impurities were re-purified by silica gel column chromatography (Merck Art. 9385: 120 g; ethyl acetate:hexane =2:3), to give methyl 7-[(1R,2R,3R,5S)-5-acetoxy-2-((E)-4,4-difluoro-3-oxo-4-phenyl-1-butenyl)-3-(2-tetrahydropyranyloxy)cyclopentyl] heptanate (7) (0.257 g; 0.467 mmol; yield: 74.4%) as a colorless oil.

$^1$H-NMR (200 MHz, CDCl$_3$): δ (ppm): 7.60-7.50 (2H, m), 7.50-7.38 (3H, m), 7.10 (0.5H, dd, J=16.7, 8.5 Hz), 7.02 (0.5H, dd, J=16.7, 9.5 Hz), 6.66 (0.5H, d, J=16.7 Hz), 6.59 (0.5H, d, J=16.7 Hz), 5.17-5.05 (1H, m), 4.55-4.48 (0.5H, m), 4.40-4.30 (0.5H, m), 4.16-3.67 (1H, m), 3.66 (3H, s), 3.58-3.13 (2H, m), 2.84-2.35 (2H, m), 2.29 (2H, t, J=7.5 Hz), 2.06 (3H, s), 1.93-1.02 (17H, m)

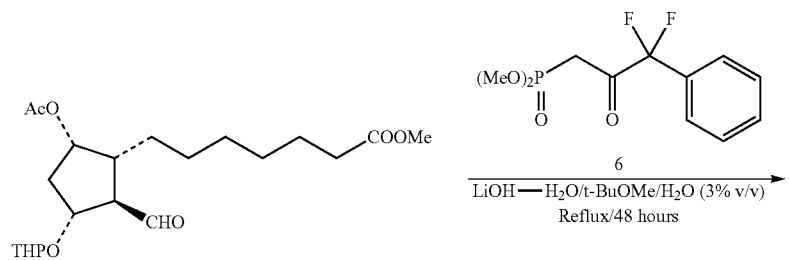

2

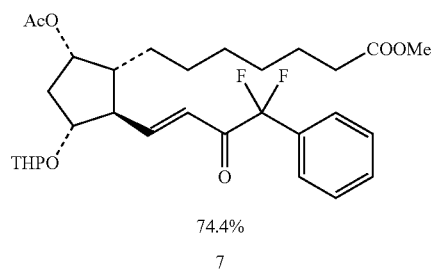

74.4%

7

Example 5c

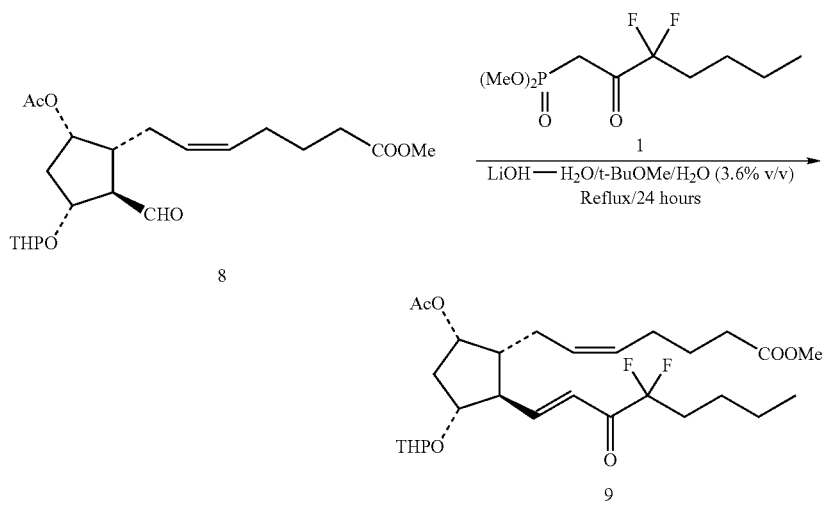

To a solution of dimethyl (3,3-difluoro-2-oxoheptyl)phosphonate (1) (1.816 g, 7.033 mmol) in t-butyl methyl ether (16 ml), lithium hydroxide monohydrate (0.271 g, 6.46 mmol) was added and the mixture was stirred for 2.25 hours at room temperature. A solution of methyl (Z)-7-[(1R,2R,3R,5S)-5-acetoxy-2-formyl-3-(2-tetrahydropyranyloxy)cyclopentyl]-5-heptenate (8) (1.554 g, 3.920 mmol) in t-butyl methyl ether (4.7 ml) and water (0.75 ml) were added thereto, and the mixed solution was heat refluxed for approximately 24 hours. After cooling to room temperature, water was added to the solution and the mixture was stirred, let to stand and then separated into two layers. The aqueous layer was extracted twice with ethyl acetate. The organic layers were combined, sequentially washed with 3% aqueous sodium chloride and saturated aqueous sodium chloride, and dried with anhydrous magnesium sulfate. After concentration under reduced pressure, the residue was purified by silica gel column chromatography (Fuji Silysia BW-300SP: 47 g, ethyl acetate:hexane =1:4), to give methyl(Z)-7-[(1R,2R,3R,5S)-5-acetoxy-2-((E)-4,4-difluoro-3-oxo-1-octenyl)-3-(2-tetrahydropyranyloxy)cyclopentyl]-5-heptenate (9) (1.787 g; 3.380 mmol; yield: 86.2%) as a pale yellow oil.

$^1$H-NMR (200 MHz, CDCl$_3$): δ (ppm): 7.11 (0.5H, dd, J=15.7, 7.6 Hz), 7.08 (0.5H, dd, J=15.7, 6.9 Hz), 6.68 (0.5H, d, J=15.7 Hz), 6.63 (0.5H, d, J=15.7 Hz), 5.45-5.21 (2H, m), 5.15-5.05 (1H, m), 4.62-4.44 (1H, m), 4.19-3.96 (1H, m), 3.88-3.62 (1H, m), 3.66 (3H, s), 3.52-3.32 (1H, m), 2.92-2.36 (2H, m), 2.29 (2H, t, J=7.3 Hz), 2.23-1.22 (22H, m), 2.07 (3H, s), 0.92 (3H, t, J=6.9 Hz)

Example 6

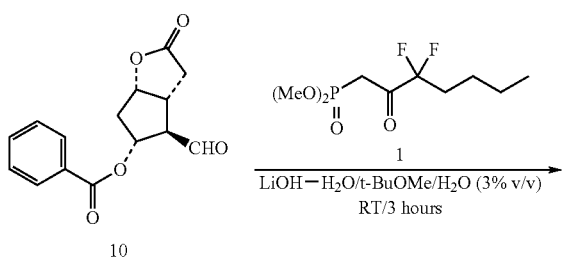

-continued

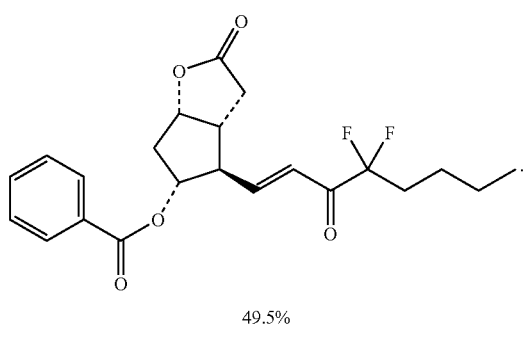

49.5%

11

To a solution of dimethyl (3,3-difluoro-2-oxoheptyl)phosphonate (1) (0.378 g, 1.50 mmol) in t-butyl methyl ether (5 ml), lithium hydroxide monohydrate (60.8 mg, 1.45 mmol) was added and the mixture was stirred for one hour at room temperature. Water (0.15 ml) and (3aR,4R,5R,6aS)-2-oxo-5-phenylcarbonyloxyhexahydro cyclopenta[b]furan-4-carbaldehyde (10) (0.274 g, 1.00 mmol) were added thereto and the mixed solution was stirred for approximately 3 hours at room temperature. The reaction mixture was added to water and extracted twice with t-butyl methyl ether. The organic layers were combined, sequentially washed with water, saturated sodium bicarbonate water and saturated aqueous sodium chloride, and then dried with anhydrous magnesium sulfate. After concentration under reduced pressure, the residue was purified by silica gel column chromatography (Fuji Silysia BW-300: 100 g; ethyl acetate:hexane =1:2), to give (3aR,4R,5R,6aS)-4-((E)-4,4-difluoro-3-oxo-1-octenyl)-2-oxo-5-phenylcarbonyloxyhexahydrocyclopenta[b]furan (11) (0.201 g; 0.495 mmol; yield: 49.5%) as a colorless oil.

$^1$H-NMR (200 MHz, CDCl$_3$): δ (ppm): 8.03-7.95 (2H, m), 7.63-7.39 (3H, m), 7.03 (1H, dd, J=15.8, 7.7 Hz), 6.66 (1H, d, J=15.8 Hz), 5.30-5.41 (1H, m), 5.20-5.06 (1H, m), 3.08-2.82 (3H, m), 2.74-2.26 (3H, m), 2.15-1.81 (2H, m), 1.54-1.20 (4H, m), 0.89 (3H, t, J=7.0 Hz)

Comparative Example 6

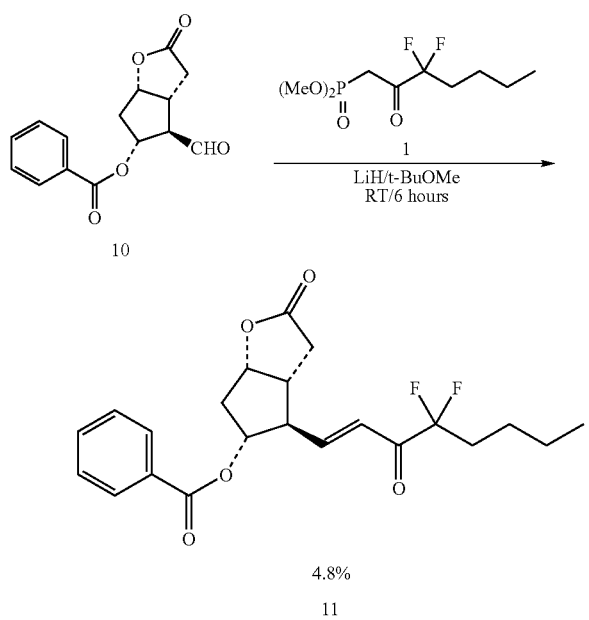

4.8%

11

To a solution of dimethyl (3,3-difluoro-2-oxoheptyl)phosphonate (1) (0.969 g, 3.75 mmol) in anhydrous t-butyl methyl ether (15 ml), lithium hydride (28.6 mg, 3.60 mmol) was added and the mixture was stirred for two hours at room temperature. (3aR,4R,5R,6aS)-2-oxo-5-phenyl carbonyloxyhexahydrocyclopenta[b]furan-4-carbaldehyde (10) (0.686 g, 2.50 mmol) was added thereto and the mixed solution was stirred for approximately 6 hours at room temperature. Water was added to the solution and the mixture was stirred, let to stand and then separated into two layers. The aqueous layer was extracted twice with ethyl acetate. The organic layers were combined, sequentially washed with 3% aqueous sodium chloride and saturated aqueous sodium chloride, and then dried with anhydrous magnesium sulfate. After concentration under reduced pressure, the residue was purified by silica gel column chromatography (Fuji Silysia BW-300SP: 28 g; ethyl acetate:hexane =1:2) to give (3aR,4R, 5R,6aS)-4-((E)-4,4-difluoro-3-oxo-1-octenyl)-2-oxo-5-phenylcarbonyloxyhexahydrocyclopenta[b]furan (11) (48.5 mg; 0.119 mmol; yield: 4.8%).

Example 7

To a solution of dimethyl (2-oxoheptyl)phosphonate (12) (0.178 g, 0.801 mmol) in t-butyl methyl ether (2 ml), lithium hydroxide monohydrate (32.5 mg, 0.775 mmol) was added and the mixture was stirred for two hours at room temperature. A solution of methyl 7-[(1R,2R,3R,5S)-5-acetoxy-2-formyl-3-(2-tetrahydropyranyloxy)cyclopentyl]heptanate (2) (0.213 g, 0.535 mmol) in t-butyl methyl ether (2 ml) and water (0.12 ml) were added thereto, and the mixed solution was stirred for one hour at room temperature. The reaction mixture was added to water and extracted twice with t-butyl methyl ether. The organic layers were combined, sequentially washed with saturated sodium bicarbonate water and saturated aqueous sodium chloride, and then dried with anhydrous magnesium sulfate. After concentration under reduced pressure, the residue was purified by silica gel column chromatography (Fuji Silysia BW-300: 100 g; ethyl acetate:hexane =3:7), to give methyl 7-[(1R,2R,3R,5S)-5-acetoxy-2-((E)-3-oxo-1-octenyl)-3-(2-tetrahydropyranyloxy)cyclopentyl]heptanate (13) (0.255 g; 0.516 mmol; yield: 96.4%) as a colorless oil.

$^1$H-NMR (200 MHz, CDCl$_3$): δ (ppm): 6.71 (0.5H, dd, J=16, 7.5 Hz), 6.68 (0.5H, dd, J=16, 7.5 Hz), 6.22 (0.5H, d, J=16 Hz), 6.20 (0.5H, d, J=16 Hz), 5.19-5.08 (1H, m), 4.61-4.52 (1H, m), 4.15-3.95 (1H, m), 3.90-3.60 (1H, m), 3.66 (3H, s), 3.50-3.35 (1H, m), 2.75-2.35 (2H, m), 2.65 (2H, t, J=7.0 Hz), 2.29 (2H, t, J=7.5 Hz), 2.06 (3H, s), 1.90-1.15 (23H, m), 0.90 (3H, t, J=7.5 Hz)

Example 8

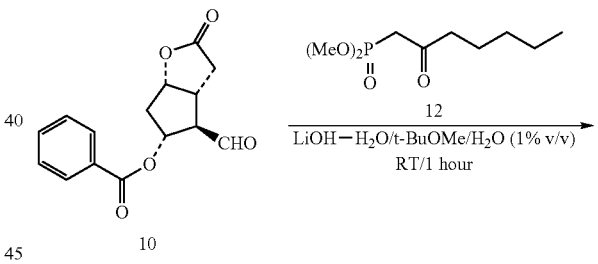

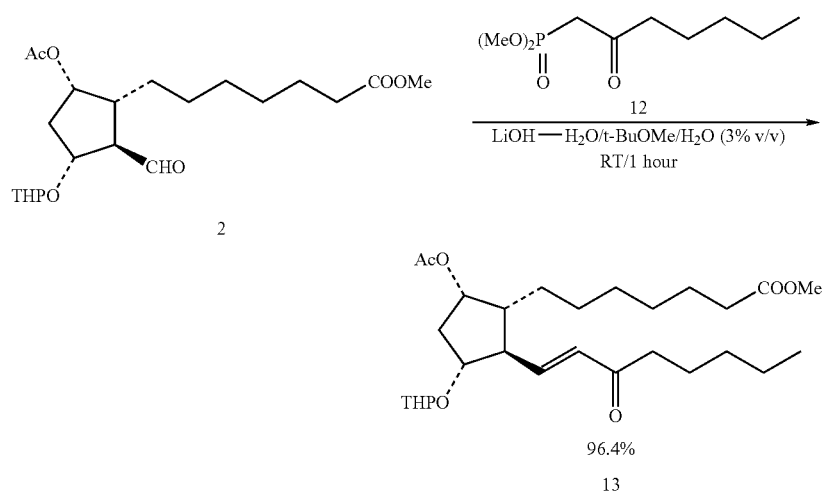

96.4%

13

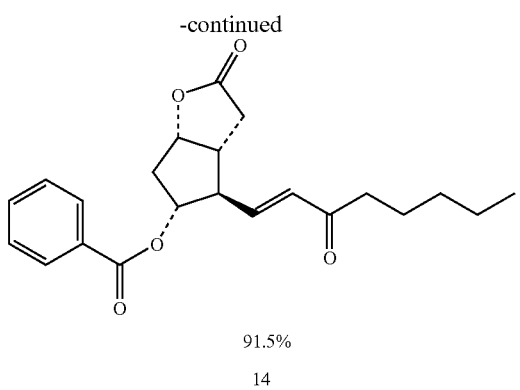

91.5%

14

To a solution of dimethyl (2-oxoheptyl)phosphonate (12) (0.267 g, 1.20 mmol) in t-butyl methyl ether (5 ml), lithium hydroxide monohydrate (48.3 mg, 1.15 mmol) was added, and the mixture was stirred for one hour at room temperature. Water (0.05 ml) and (3aR,4R,5R,6aS)-2-oxo-5-phenylcarbonyloxyhexahydro cyclopenta[b]furan-4-carbo aldehyde (10) (0.274 g, 1.00 mmol) were added thereto, and the mixed solution was stirred for one hour at room temperature. The reaction mixture was added to water and washed twice with t-butyl methyl ether. The organic layers were combined, sequentially washed with saturated sodium bicarbonate water and saturated aqueous sodium chloride, and then dried with anhydrous magnesium sulfate. After concentration under reduced pressure, the residue was purified by silica gel column chromatography (Fuji Silysia BW-300: 100 g; ethyl acetate:hexane =2:3) to give (3aR,4R,5R,6aS)-4-((E)-3-oxo-1-octenyl)-2-oxo-5-phenyl carbonyloxyhexahydrocyclopenta[b]furan (14) (0.339 g; 0.915 mmol; yield: 91.5%) as a colorless oil.

$^1$H-NMR (200 MHz, CDCl$_3$): δ (ppm): 8.05-7.95 (2H, m), 7.65-7.40 (3H, m), 6.73 (1H, dd, J=16, 7.5 Hz), 6.37 (1H, dd, J=16 Hz), 5.42-5.28 (1H, m), 5.19-5.06 (1H, m), 3.00-2.45 (5H, m), 2.55 (2H, J=7.0 Hz), 2.38-2.25 (1H, m), 1.70-1.54 (2H, m), 1.90-1.20 (4H, m), 0.90 (3H, t, J=7.5 Hz)
(Application of the Method for the Invention)

Using the method of the invention, a therapeutically useful compound was prepared.

To a solution of dimethyl (3,3-difluoro-2-oxoheptyl)phosphonate (1) (69.65 g, 269.8 mmol) in t-butyl methyl ether (1046 ml), lithium hydroxide monohydrate (10.69 g, 254.8 mmol) was added and the mixture was stirred for one hour at room temperature. A solution of methyl 7-[(1R,2R,3R,5S)-5-acetoxy-2-formyl-3-(2-tetrahydropyranyloxy)cyclopentyl]heptanate (2) (59.72 g, 149.9 mmol) in t-butyl methyl ether (233 ml) and water (20.2 ml) were added thereto, and the mixed solution was heat refluxed for approximately 41 hours (internal temperature: approximately 54° C.). After cooling to room temperature, water (351 ml) was added to the solution and the mixture was stirred, let to stand and then separated into two layers. The aqueous layer was extracted twice with ethyl acetate (234 ml). The organic layers were combined, washed sequentially with 3% aqueous sodium chloride (351 ml) and saturated aqueous sodium chloride (351 ml), and dried with anhydrous magnesium sulfate (55 g). After concentration under reduced pressure, the residue was purified by silica gel column chromatography (Fuji Silysia BW-300: 2280; ethyl acetate:hexane =1:4). The fractions containing impurities were re-purified by silica gel column chromatography (Fuji Silysia BW-300: 582 g; ethyl acetate:hexane =1:4) to give methyl 7-[(1R,2R,3R,5S)-5-acetoxy-2-((E)-4,4-difluoro-3-oxo-1-octenyl)-3-(2-tetrahydropyranyloxy)cyclopentyl]heptanate (3) (71.02 g; 133.8 mmol; yield: 89.3%) as a pale yellow oil.

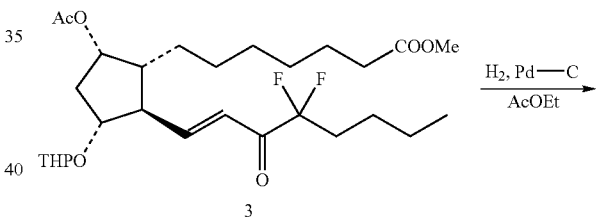

3

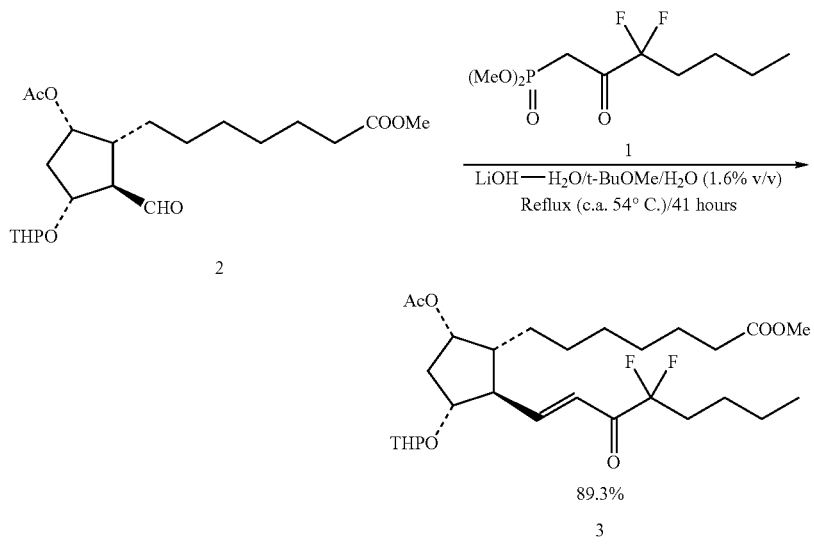

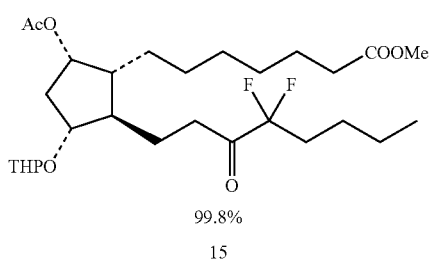

99.8%

15

To a solution of methyl 7-[(1R,2R,3R,5S)-5-acetoxy-2-((E)-4,4-difluoro-3-oxo-1-octenyl)-3-(2-tetrahydropyranyloxy)cyclopentyl]heptanate (3) (70.90 g, 133.6 mmol) in ethyl acetate (357 ml), 5%-palladium on carbon (7.12 g) was added and the solution was hydrogenated at room temperature and the ambient pressure. The reaction mixture was filtered, the filtrate was concentrated under reduced pressure to give methyl 7-[(1R,2R,3R,5S)-5-acetoxy-2-(4,4-difluoro-3-oxooctyl)-3-(2-tetrahydropyranyloxy)cyclopentyl]heptanate (15) (71.02 g; 133.3 mmol; yield: 99.8%) as a colorless oil.

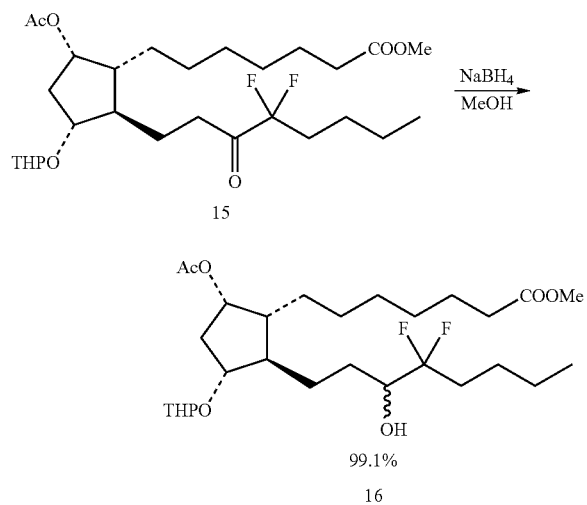

15

99.1%

16

A solution of methyl 7-[(1R,2R,3R,5S)-5-acetoxy-2-(4,4-difluoro-3-oxooctyl)-3-(2-tetrahydro pyranyloxy)cyclopentyl]heptanate (15) (71.01 g, 133.3 mmol) in methanol (284 ml) was cooled to approximately −20° C., and sodium borohydride (5.08 g, 134 mmol) was added thereto. After stirring for approximately 40 minutes, acetic acid (7.6 ml, 133 mmol) was added drop wise, and the reaction mixture was concentrated under reduced pressure. The residue was supplemented with water (325 ml) and extracted three times with ethyl acetate (228 mL). The organic layers were combined, washed with 3% aqueous sodium chloride (325 ml) and saturated aqueous sodium chloride (325 ml), and dried with anhydrous magnesium sulfate (51 g). The solution was concentrated under reduced pressure to give methyl 7-[(1R,2R,3R,5S)-5-acetoxy-2-(4,4-difluoro-3-hydroxyoctyl)-3-(2-tetrahydropyranyloxy)cyclopentyl]heptanate (16) (70.64 g; 132.1 mmol; yield: 99.1%) as a colorless oil.

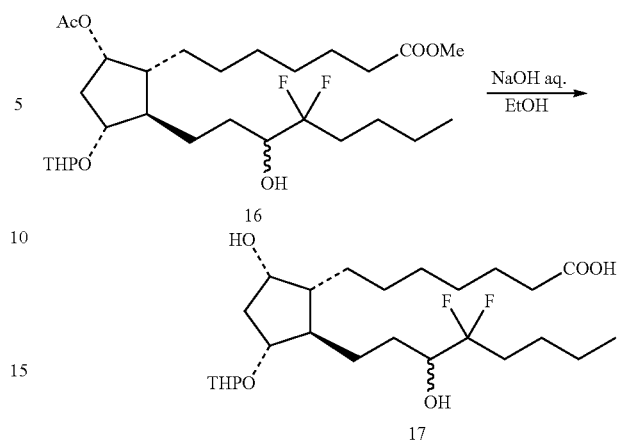

16

17

A solution of methyl 7-[(1R,2R,3R,5S)-5-acetoxy-2-(4,4-difluoro-3-hydroxyoctyl)-3-(2-tetrahydropyranyloxy)cyclopentyl]heptanate (16) (70.62 g, 132.1 mmol) in ethanol (213 ml) was cooled on ice, and an 8N-sodium hydroxide aqueous solution (132 ml, 1056 mmol) was added thereto drop wise. After stirring at room temperature for approximately hours, the reaction mixture was concentrated under reduced pressure. The residue was supplemented with water (280 ml) and t-butyl methyl ether (141 ml), and cooled on ice. After 6N-hydrochloric acid was added drop wise to adjust to pH 3 to 4, the solution was extracted three times with ethyl acetate (280 ml). The organic layers were combined and sequentially washed with water (280 ml) twice and saturated aqueous sodium chloride (336 ml). After drying with anhydrous magnesium sulfate (50 g), the solution was concentrated under reduced pressure to give crude 7-[(1R,2R,3R,5S)-2-(4,4-difluoro-3-hydroxyoctyl)-5-hydroxy-3-(2-tetrahydropyranyloxy)cyclopentyl]heptanoic acid (17) as white solid. The entire amount was used in the following step without purification.

$^1$H-NMR (200 MHz, CDCl$_3$): δ (ppm): 4.71-4.58 (1H, m), 4.18-3.96 (2H, m), 3.96-3.60 (2H, m), 3.60-3.42 (1H, m), 2.35 (2H, t, J=7.5 Hz), 2.13-1.17 (30H, m), 0.93 (3H, t, J=7.1 Hz)

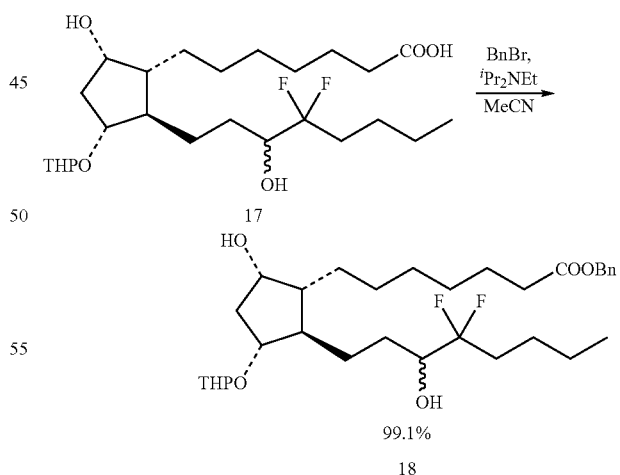

17

18

99.1%

To the crude 7-[(1R,2R,3R,5S)-2-(4,4-difluoro-3-hydroxyoctyl)-5-hydroxy-3-(2-tetrahydropyranyloxy)cyclopentyl]heptanoic acid (17) (132.1 mmol) in acetonitrile (315 ml), diisopropyl ethylamine (69.0 ml, 369 mmol) and benzyl bromide (47.1 ml, 369 mmol) were added and the mixture was stirred for 14 hours at room temperature. The reaction mixture was concentrated under reduced pressure, ethyl acetate (366 ml) and water (280 ml) were added to the residue and the mixture was stirred, let to stand and then separated into two layers. The aqueous layer was extracted twice with ethyl acetate (224 ml). The organic layers were combined and washed with 1N-hydrochloric acid (336 ml), saturated sodium bicarbonate water (336 ml) and saturated aqueous sodium chloride (336 ml). After drying with anhydrous magnesium sulfate (51 g), the solution was concentrated under reduced pressure. The concentration residue was purified by silica gel column chromatography (Fuji Silysia BW-300: 2400 g; ethyl acetate:hexane =1:2) to give benzyl 7-[(1R,2R,3R,5S)-2-(4,4-difluoro-3-hydroxyoctyl)-5-hydroxy-3-(2-tetrahydropyranyloxy)cyclopentyl]heptanate (18) (74.44 g; 130.9 mmol; yield: 99.1%) as a colorless oil.

$^1$H-NMR (200 MHz, CDCl$_3$): δ (ppm): 7.42-7.26 (5H, m), 5.11 (2H, s), 4.70-4.57 (1H, m), 4.18-3.96 (2H, m), 3.96-3.58 (2H, m), 3.58-3.42 (1H, m), 2.51-2.21 (2H, m), 2.35 (2H, t, J=7.4 Hz), 2.16-1.12 (29H, m), 0.93 (3H, t, J=7.1 Hz)

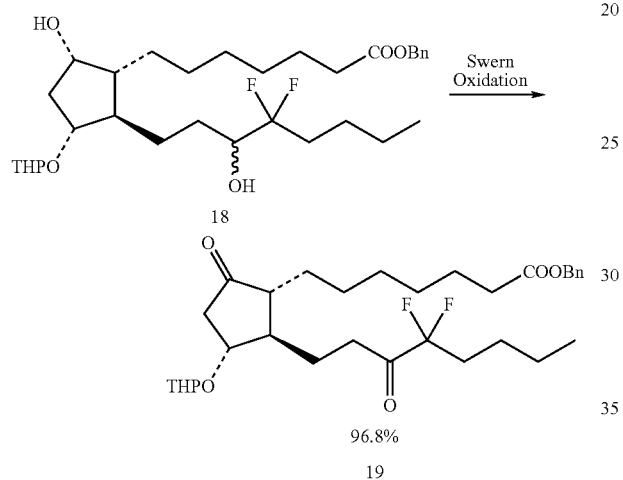

A solution of oxalyl chloride (57.0 ml, 653 mmol) in dichloromethane (635 ml) was cooled in a dry ice-methanol bath. Dimethylsulfoxide (92.7 ml, 1306 mmol) was added drop wise and the solution was stirred for 30 minutes. A solution of benzyl 7-[(1R,2R,3R,5S)-2-(4,4-difluoro-3-hydroxyoctyl)-5-hydroxy-3-(2-tetrahydropyranyloxy)cyclopentyl]heptanate (18) (74.31 g, 130.7 mmol) in dichloromethane (191 ml) was added drop wise, and the mixture was stirred for approximately 1.5 hours. Triethylamine (273 ml, 1959 mmol) was added drop wise to the mixture and the reaction mixture was warmed to 0° C., saturated ammonium water (605 ml) was added to the solution and the mixture was stirred, let to stand and then separated into two layers. The aqueous layer was extracted twice with dichloromethane (302 ml). The organic layers were combined and sequentially washed with 0.35N-hydrochloric acid (302 ml), water (605 ml), saturated sodium bicarbonate water (605 ml) and saturated aqueous sodium chloride (605 ml). After drying with anhydrous magnesium sulfate (52 g), the solution was concentrated under reduced pressure. The residue was dissolved in a suitable amount of ethyl acetate/hexane solvent mix (1:10), and insoluble matter was filtered. The filtrate was concentrated under reduced pressure and the residue was purified by silica gel column chromatography (Fuji Silysia BW-300: 2260 g; ethyl acetate:hexane =1:4) to give benzyl 7-[(1R,2R,3R)-2-(4,4-difluoro-3-oxooctyl)-5-oxo-3-(2-tetrahydropyranyloxy)cyclopentyl]heptanate (19) (71.44 g; 126.5 mmol; yield: 96.8%) as a pale yellow oil.

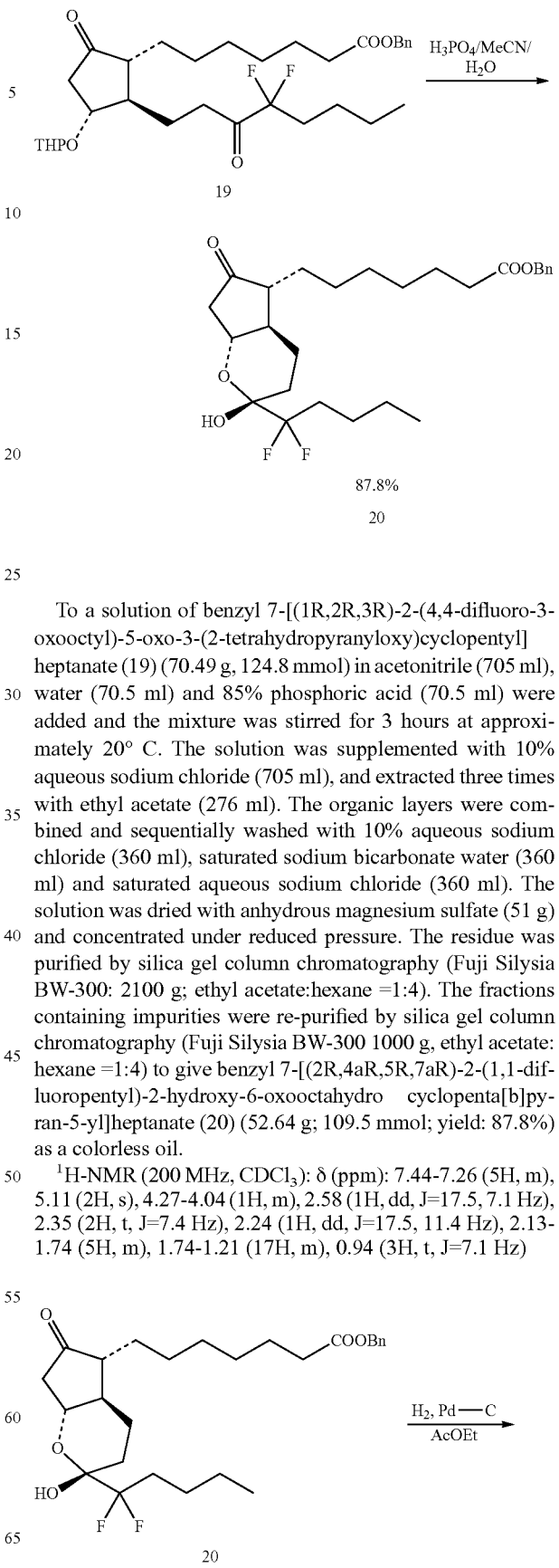

To a solution of benzyl 7-[(1R,2R,3R)-2-(4,4-difluoro-3-oxooctyl)-5-oxo-3-(2-tetrahydropyranyloxy)cyclopentyl] heptanate (19) (70.49 g, 124.8 mmol) in acetonitrile (705 ml), water (70.5 ml) and 85% phosphoric acid (70.5 ml) were added and the mixture was stirred for 3 hours at approximately 20° C. The solution was supplemented with 10% aqueous sodium chloride (705 ml), and extracted three times with ethyl acetate (276 ml). The organic layers were combined and sequentially washed with 10% aqueous sodium chloride (360 ml), saturated sodium bicarbonate water (360 ml) and saturated aqueous sodium chloride (360 ml). The solution was dried with anhydrous magnesium sulfate (51 g) and concentrated under reduced pressure. The residue was purified by silica gel column chromatography (Fuji Silysia BW-300: 2100 g; ethyl acetate:hexane =1:4). The fractions containing impurities were re-purified by silica gel column chromatography (Fuji Silysia BW-300 1000 g, ethyl acetate: hexane =1:4) to give benzyl 7-[(2R,4aR,5R,7aR)-2-(1,1-difluoropentyl)-2-hydroxy-6-oxooctahydro cyclopenta[b]pyran-5-yl]heptanate (20) (52.64 g; 109.5 mmol; yield: 87.8%) as a colorless oil.

$^1$H-NMR (200 MHz, CDCl$_3$): δ (ppm): 7.44-7.26 (5H, m), 5.11 (2H, s), 4.27-4.04 (1H, m), 2.58 (1H, dd, J=17.5, 7.1 Hz), 2.35 (2H, t, J=7.4 Hz), 2.24 (1H, dd, J=17.5, 11.4 Hz), 2.13-1.74 (5H, m), 1.74-1.21 (17H, m), 0.94 (3H, t, J=7.1 Hz)

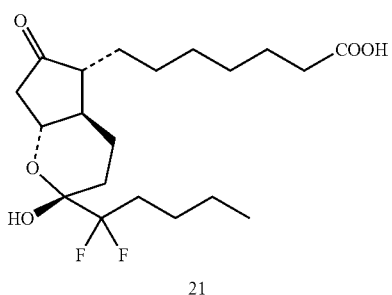

21

To a solution of benzyl 7-[(2R,4aR,5R,7aR)-2-(1,1-difluoropentyl)-2-hydroxy-6-oxooctahydrocyclopenta[b]pyran-5-yl]heptanate (20) (51.88 g, 108.0 mmol) in ethyl acetate (521 ml), 10%-palladium on carbon (50% hydrous, 7.81 g) was added, and the solution was hydrogenated at ambient pressure and at approximately 20° C. The reaction mixture was filtered through celite, and the filtrate was concentrated under reduced pressure. The concentration residue was purified by silica gel column chromatography (Fuji Silysia FL-60D: 1156 g; ethyl acetate:hexane=1:2) to give a white solid (44.67 g). This solid was dissolved in ethyl acetate, and hexane was added drop wise to recrystallize the compound. Recrystallization was carried out twice, to give purified white crystal (36.42 g). The crystal was dissolved in ethyl acetate, and filtered through a membrane filter. Hexane was added to the filtrate to recrystallize. The crystal was recovered by filtration and vacuum dried to give 7-[(2R,4aR,5R,7aR)-2-(1,1-difluoropentyl)-2-hydroxy-6-oxooctahydro cyclopenta[b]pyran-5-yl]heptane acid (21) (35.30 g; 90.41 mmol; yield: 83.7%), which is a compound that is useful as a pharmaceutical agent.

(Preparation of Starting Material)

The aldehyde (2) used in the present invention was prepared by the following method.

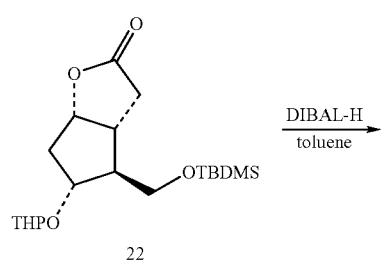

A solution of (3aR,4S,5R,6aS)-4-(t-butyldimethyl silyloxymethyl)-5-(2-tetrahydropyranyloxy)hexahydrocyclopenta[b]furan-2-one (22) (96.7 g, 261 mmol) in toluene (600 ml) was cooled to −75° C. 1.5M-diisobutyl aluminum hydride (261 ml, 392 mmol) was added thereto drop wise and the mixture was stirred at −78° C. for approximately 2 hours. After adding methanol (69.0 ml, 1703 mmol) drop wise to the solution, the solution was warmed to room temperature. Saturated aqueous potassium sodium tartrate (800 ml) and diethyl ether (400 ml) were added thereto and the mixture was stirred for one hour, let to stand and then separated into two layers. The aqueous layer was extracted twice with diethyl ether (400 ml). The organic layers were combined, washed twice with saturated aqueous sodium chloride (800 ml) and then dried with anhydrous magnesium sulfate. The solution was concentrated under reduced pressure to give (3aR,4S,5R,6aS)-4-(t-butyldimethylsilyl oxymethyl)-5-(2-tetrahydropyranyloxy) hexahydrocyclopenta[b]furan-2-ol (23) (97.8 g, quantitatively) as a slightly yellow oil.

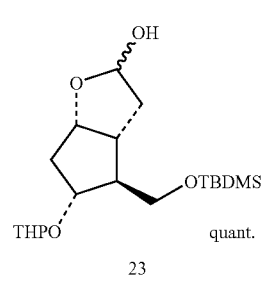

A suspension of (4-carboxy butyl) triphenyl phosphonium bromide (289.3 g, 652.6 mmol) in tetrahydrofuran (1000 ml) was cooled on ice. To the suspension, potassium t-butoxide (146.3 g, 1304 mmol) was added and the mixture was warmed to room temperature. A solution of (3aR,4S,5R,6aS)-4-(t-butyldimethylsilyloxymethyl)-5-(2-tetrahydropyranyloxy) hexahydrocyclopenta[b]furan-2-ol (23) (97.2 g, 261 mmol) in tetrahydrofuran (500 ml) was added, and the resulting solution was stirred for approximately 1.5 hours. Ice water (800 ml) was added to the reaction and the mixture was concentrated under reduced pressure. Then, ice-cooled 1N-hydrochloric acid (600 ml) and ethyl acetate (800 ml) were added to the residue and the mixture was stirred, let to stand and then separated into two layers. The aqueous layer was extracted twice with ethyl acetate (400 ml). The organic layers were combined, and washed with saturated aqueous sodium chloride (800 ml). After drying with anhydrous magnesium sulfate, the solution was concentrated under reduced pressure, diethyl ether (1400 ml) was added to the residue and the mixture was stirred for 30 minutes. The resulting mixture was filtered, and the deposited white solid was eliminated. The filtrate was concentrated under reduced pressure to give crude (Z)-7-[(1R,2S,3R,5S)-2-(t-butyldimethylsilyloxymethyl)-5-hydroxy-3-(2-tetrahydropyranyloxy)cyclopentyl]-5-heptenoic acid (24) (220 g) as white solid. The entire amount was used in the following step without purification.

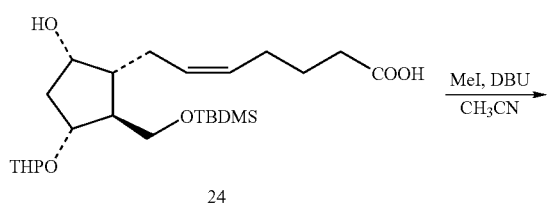

24

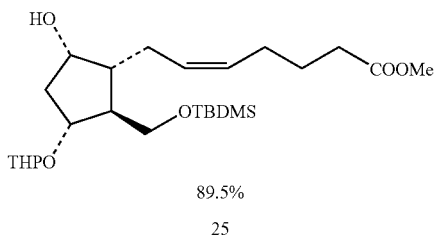

89.5%

25

A solution of (Z)-7-[(1R,2S,3R,5S)-2-(t-butyldimethylsilyloxymethyl)-5-hydroxy-3-(2-tetrahydropyranyloxy)cyclopentyl]-5-heptenoic acid (24) (261 mmol) in acetonitrile (1000 ml) was cooled on ice. Diazabicycloundecene (156.0 ml, 1044 mmol) was added thereto and methyl iodide (65.0 ml, 1044 mmol) was added drop wise to the solution. The reaction mixture was warmed to room temperature, and stirred for 14 hours. The reaction mixture was cooled on ice, diazabicycloundecene (39.0 ml, 261 mmol) and methyl iodide (16.3 ml, 261 mmol) were added, then, the mixture was stirred at room temperature for 1.25 hours. The reaction mixture was again cooled on ice, and diazabicycloundecene (39.0 ml, 261 mmol) and methyl iodide (16.3 ml, 261 mmol) were added. After stirring at room temperature for one hour, the reaction mixture was concentrated under reduced pressure. Ethyl acetate (400 ml) and water (400 ml) were added to the residue and the mixture was stirred, let to stand and then separated into two layers. The aqueous layer was extracted twice with ethyl acetate (400 ml), the organic layers were combined and sequentially washed with 1N-hydrochloric acid (600 ml), saturated sodium bicarbonate water (800 ml) and saturated aqueous sodium chloride (800 ml). After drying with anhydrous magnesium sulfate, the solution was concentrated under reduced pressure. The residue was purified by silica gel column chromatography (Fuji Silysia BW-300: 2000 g; ethyl acetate:hexane =1:3), the fractions containing impurities were re-purified by silica gel column chromatography (Fuji Silysia BW-300: 190 g; ethyl acetate:hexane = 1:3) to give methyl (Z)-7-[(1R,2S,3R,5S)-2-(t-butyldimethylsilyloxymethyl)-5-hydroxy-3-(2-tetrahydropyranyloxy)cyclopentyl]-5-heptenate (25) (110.4 g, 233.5 mmol, 89.5%) as colorless oil.

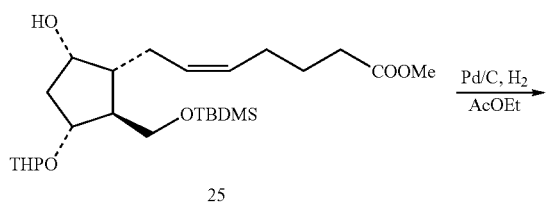

25

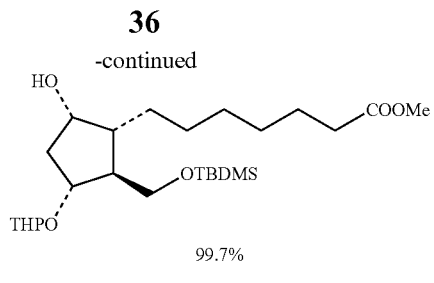

99.7%

26

To a solution of methyl (Z)-7-[(1R,2S,3R,5S)-2-(t-butyldimethylsilyloxymethyl)-5-hydroxy-3-(2-tetrahydropyranyloxy)cyclopentyl]-5-heptenate (25) (109.9 g, 233.5 mmol) in ethyl acetate (450 ml), 5%-palladium on carbon (10.98 g) was added and the mixture was hydrogenated at ambient pressure and at room temperature. The reaction mixture was filtered and the filtrate was concentrated under reduced pressure to give methyl 7-[(1R,2S,3R,5S)-2-(t-butyldimethylsilyloxymethyl)-5-hydroxy-3-(2-tetrahydropyranyloxy)cyclopentyl]heptanate (26) (110.1 g, 232.9 mmol, 99.7%) as colorless oil.

$^1$H-NMR (200 MHz, CDCl$_3$): δ (ppm): 4.75-4.65 (1H, m), 4.26-4.06 (2H, m), 3.97-3.28 (4H, m), 3.67 (3H, s), 2.52 (0.5H, d, J=10.1 Hz), 2.39 (0.5H, d, J=10.1 Hz), 2.31 (2H, t, J=7.5 Hz), 2.10-1.18 (19H, m), 0.89 (4.5H, s), 0.88 (4.5H, s), 0.04 (6H, s).

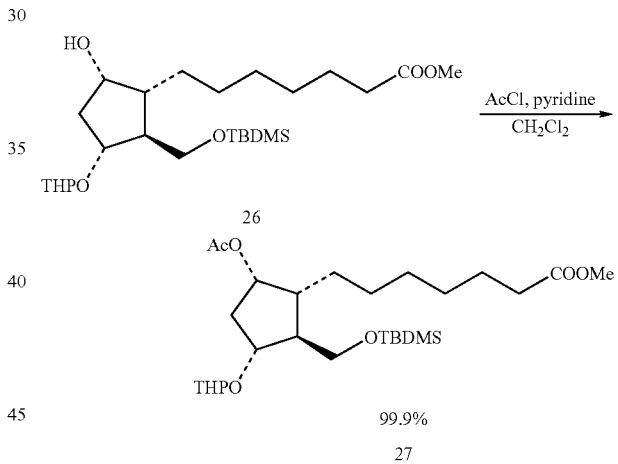

A solution of methyl 7-[(1R,2S,3R,5S)-2-(t-butyldimethylsilyloxymethyl)-5-hydroxy-3-(2-tetrahydropyranyloxy)cyclopentyl]heptanate (26) (109.6 g, 231.8 mmol) in dichloromethane (500 ml) was cooled on ice. Pyridine (28.1 ml, 347 mmol) and acetyl chloride (24.0 ml, 349 mmol) were added drop wise to the solution, and the solution was stirred at room temperature for 1.5 hours. Water (600 ml) was added to the solution and the mixture was stirred, let to stand, separated into two layers, and the aqueous layer was extracted twice with dichloromethane (400 ml). The organic layers were combined and washed with 1N-hydrochloric acid (600 ml), saturated sodium bicarbonate water (800 ml) and saturated aqueous sodium chloride (800 ml). After drying with anhydrous magnesium sulfate, the solution was concentrated under reduced pressure to give methyl 7-[(1R,2S,3R,5S)-5-acetoxy-2-(t-butyldimethylsilyloxymethyl)-3-(2-tetrahydropyranyloxy)cyclopentyl]heptanate (27) (119.2 g, 231.5 mmol, 99.9%), as slightly yellow oil.

$^1$H-NMR (200 MHz, CDCl$_3$): δ (ppm): 5.15-5.05 (1H, m), 4.76-4.53 (1H, m), 4.21-4.10 (0.5H, m), 4.10-3.95 (0.5H, m), 3.95-3.39 (4H, m), 3.67 (3H, s), 2.38-1.04 (20H, m), 2.30 (2H, t, J=7.5 Hz), 2.04 (3H, s), 0.89 (4.5H, s), 0.88 (4.5H, s), 0.04 (6H, s)

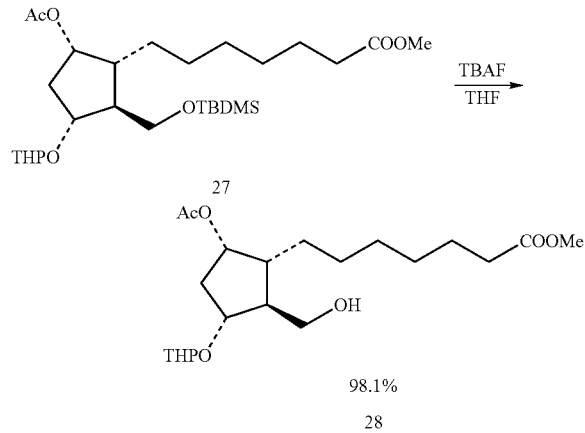

27

28

98.1%

A solution of methyl 7-[(1R,2S,3R,5S)-5-acetoxy-2-(t-butyldimethylsilyloxymethyl)-3-(2-tetrahydropyranyloxy)cyclopentyl]heptanate (27) (118.7 g, 230.6 mmol) in tetrahydrofuran (450 ml) was cooled on ice. A solution of 1M-tetra butyl ammonium fluoride (in THF, 277 ml, 277 mmol) was added drop wise thereto and the mixture was stirred at room temperature for 20.5 hours. The reaction mixture was concentrated under reduced pressure, and the residue was purified by silica gel column chromatography (Fuji Silysia BW-300: 2000 g; ethyl acetate:hexane =1:1). The fractions containing impurities were re-purified by silica gel column chromatography (Fuji Silysia BW-300: 520 g; ethyl acetate:hexane =1:1) to give methyl 7-[(1R,2S,3R,5S)-5-acetoxy-2-hydroxymethyl-3-(2-tetrahydropyranyloxy)cyclopentyl]heptanate (28) (90.64 g, 226.3 mmol, 98.1%) as colorless oil.

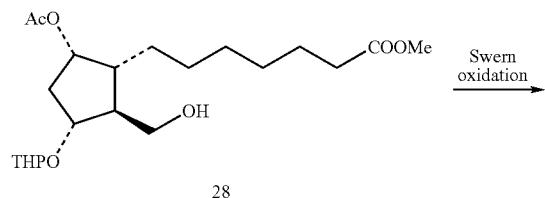

28

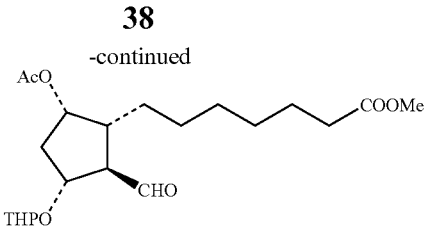

92.4%

2

A solution of oxalyl chloride (28.3 ml, 324 mmol) in dichloromethane (325 ml) was cooled in a dry ice-methanol bath. Dimethylsulfoxide (46.0 ml, 648 mmol) was added drop wise and the mixture was stirred for approximately 30 minutes. A solution of methyl 7-[(1R,2S,3R,5S)-5-acetoxy-2-hydroxymethyl-3-(2-tetrahydropyranyloxy)cyclopentyl]heptanate (28) (65.00 g, 162.3 mmol) in dichloromethane (170 ml) was added thereto drop wise and the mixture was stirred for approximately 1.5 hours. Triethylamine (113 ml, 811 mmol) was added drop wise to the reaction and the reaction mixture was warmed to 0° C. Water (426 ml) was added to the reaction mixture and the mixture was stirred, let to stand and then separated into two layers. The aqueous layer was extracted twice with t-butyl methyl ether (266 ml). The organic layers were combined and sequentially washed with 1N-hydrochloric acid (390 ml), water (426 ml), saturated sodium bicarbonate water (426 ml) and saturated aqueous sodium chloride (426 ml). After drying with anhydrous magnesium sulfate (54 g), the solution was concentrated under reduced pressure. The residue was purified by silica gel column chromatography (Fuji Silysia BW-300: 1950 g; ethyl acetate:hexane =3:7) to give methyl 7-[(1R,2R,3R,5S)-5-acetoxy-2-formyl-3-(2-tetrahydropyranyloxy)cyclopentyl]heptanate (2) (59.74 g, 149.9 mmol; yield: 92.4%) as yellow oil.

What is claimed is:

1. Methyl 7-[(1R, 2S, 3R, 5S)-2-(t-butyldimethylsilyloxymethyl)-5-hydroxy-3-(2-tetrahydropyranyloxy) cyclopentyl]heptanate.

2. Methyl 7-[(1R, 2S, 3R, 5S)-5-acetoxy-2-(t-butyl dimethylsilyloxymethyl)-3-(2-tetrahydropyranyloxy) cyclopentyl]heptanate.

\* \* \* \* \*